US011491008B2

(12) United States Patent
Keränen et al.

(10) Patent No.: US 11,491,008 B2
(45) Date of Patent: Nov. 8, 2022

(54) ANNULOPLASTY DEVICE

(71) Applicant: Medtentia International Ltd Oy, Espoo (FI)

(72) Inventors: Olli Keränen, Bjärred (SE); Hans-Reinhard Zerkowski, Kreuzlingen (CH); Johannes Jung, Pforzheim (DE); Jani Virtanen, Soderkulla (FI)

( * ) Notice: Subject to any disclaimer, the term of this patent is extended or adjusted under 35 U.S.C. 154(b) by 0 days.

(21) Appl. No.: 17/625,748

(22) PCT Filed: Jul. 13, 2020

(86) PCT No.: PCT/EP2020/069804
§ 371 (c)(1),
(2) Date: Jan. 8, 2022

(87) PCT Pub. No.: WO2021/005246
PCT Pub. Date: Jan. 14, 2021

(65) Prior Publication Data
US 2022/0202570 A1 Jun. 30, 2022

Related U.S. Application Data

(60) Provisional application No. 62/872,750, filed on Jul. 11, 2019.

(51) Int. Cl.
*A61F 2/24* (2006.01)

(52) U.S. Cl.
CPC .... *A61F 2/2445* (2013.01); *A61F 2220/0016* (2013.01); *A61F 2230/0067* (2013.01); *A61F 2230/0091* (2013.01)

(58) Field of Classification Search
CPC ........ A61F 2/24; A61F 2/2442; A61F 2/2445; A61F 2/2448; A61F 2/246
See application file for complete search history.

(56) References Cited

U.S. PATENT DOCUMENTS

| 6,419,696 | B1* | 7/2002 | Ortiz | A61F 2/2448 623/2.37 |
| 6,964,684 | B2* | 11/2005 | Ortiz | A61F 2/2466 623/2.37 |
| 7,294,148 | B2* | 11/2007 | McCarthy | A61F 2/2448 623/2.38 |

(Continued)

FOREIGN PATENT DOCUMENTS

| EP | 3476366 A1 | 5/2019 |
| WO | 2019081777 A1 | 5/2019 |

*Primary Examiner* — Seema Mathew
(74) *Attorney, Agent, or Firm* — Patent Grove LLC; Tomas Friend

(57) ABSTRACT

An annuloplasty device is disclosed comprising first and second support rings having a coiled configuration, and respective first and second retention units, the first support ring transitions to the second support ring over a transition section, the transition section is adapted to be arranged at a commissure of the heart valve leaflets, the first and second support rings extend in respective first and second coil planes being essentially perpendicular to the central axis, the transition section bends at least partly along the central axis so that the first coil plane is separated a distance from the second coil plane along the central axis at the transition section.

15 Claims, 22 Drawing Sheets

(56) References Cited

U.S. PATENT DOCUMENTS

| | | | |
|---|---|---|---|
| 7,445,632 B2* | 11/2008 | McGuckin, Jr. | A61F 2/2436 623/2.37 |
| 7,942,927 B2* | 5/2011 | Kaye | A61F 2/2445 623/2.11 |
| 7,951,196 B2* | 5/2011 | McCarthy | A61F 2/2445 623/2.37 |
| 8,535,374 B2* | 9/2013 | Redmond | A61F 2/2445 623/2.37 |
| 9,011,530 B2* | 4/2015 | Reich | A61B 17/072 623/2.37 |
| 9,687,346 B2* | 6/2017 | Migliazza | A61F 2/2445 |
| 10,166,101 B2* | 1/2019 | Alfieri | A61F 2/246 |
| 10,588,742 B2* | 3/2020 | Chau | A61F 2/243 |
| 2003/0093148 A1* | 5/2003 | Bolling | A61F 2/2448 623/2.36 |
| 2004/0167620 A1* | 8/2004 | Ortiz | A61F 2/2445 623/2.11 |
| 2005/0043791 A1* | 2/2005 | McCarthy | A61M 25/001 623/2.11 |
| 2006/0100697 A1* | 5/2006 | Casanova | A61F 2/2466 623/2.37 |
| 2006/0247491 A1* | 11/2006 | Vidlund | A61F 2/2481 623/2.37 |
| 2007/0027536 A1* | 2/2007 | Mihaljevic | A61F 2/2448 623/2.37 |
| 2007/0244555 A1* | 10/2007 | Rafiee | A61F 2/2445 623/2.11 |
| 2009/0287303 A1* | 11/2009 | Carpentier | A61F 2/2448 623/2.36 |
| 2012/0071970 A1* | 3/2012 | Carpentier | A61F 2/2466 623/2.37 |
| 2014/0364945 A1* | 12/2014 | Longoria | A61F 2/2448 623/2.36 |
| 2014/0379074 A1* | 12/2014 | Spence | A61F 2/2427 623/2.11 |
| 2015/0230921 A1* | 8/2015 | Chau | A61F 2/2418 623/2.11 |
| 2016/0262741 A1* | 9/2016 | Gilmore | A61B 17/0401 |
| 2016/0367366 A1 | 12/2016 | Alfieri | |
| 2017/0273788 A1* | 9/2017 | O'Carroll | A61F 2/2454 |
| 2018/0071094 A1* | 3/2018 | Alon | A61F 2/2445 |
| 2018/0185020 A1* | 7/2018 | Deane | A61B 17/0467 |
| 2018/0185149 A1* | 7/2018 | Lansac | A61F 2/2442 |
| 2021/0059816 A1* | 3/2021 | Keränen | A61F 2/2445 |

* cited by examiner

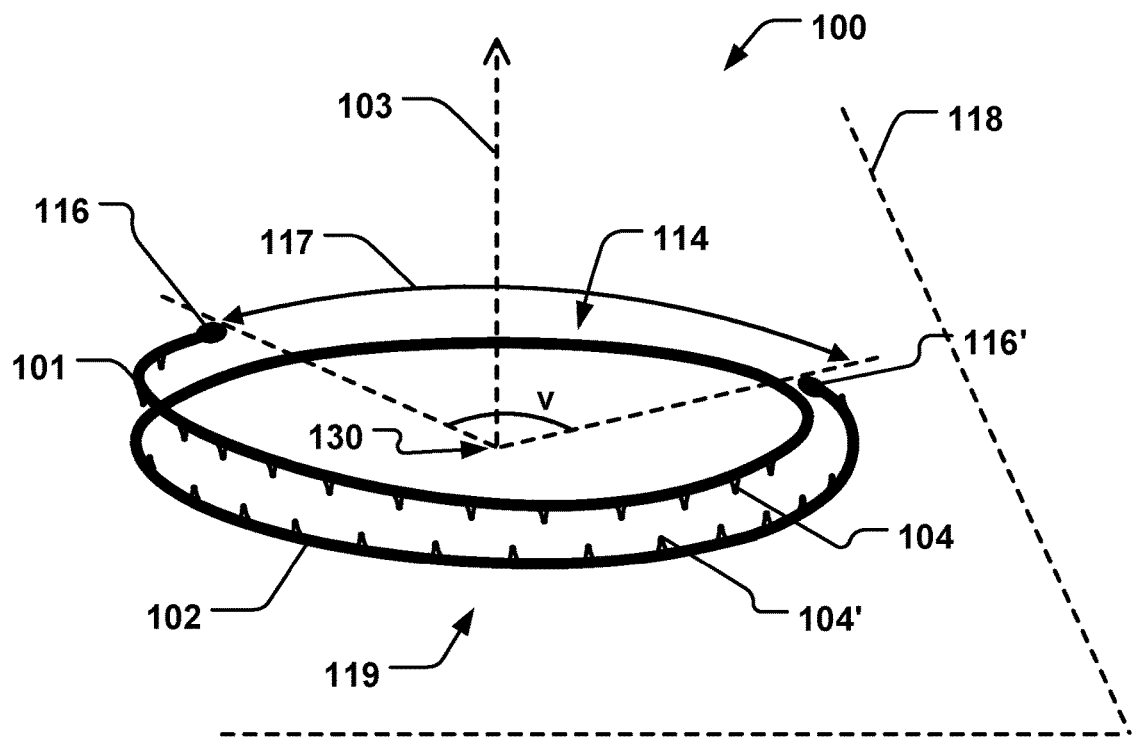
Fig. 6
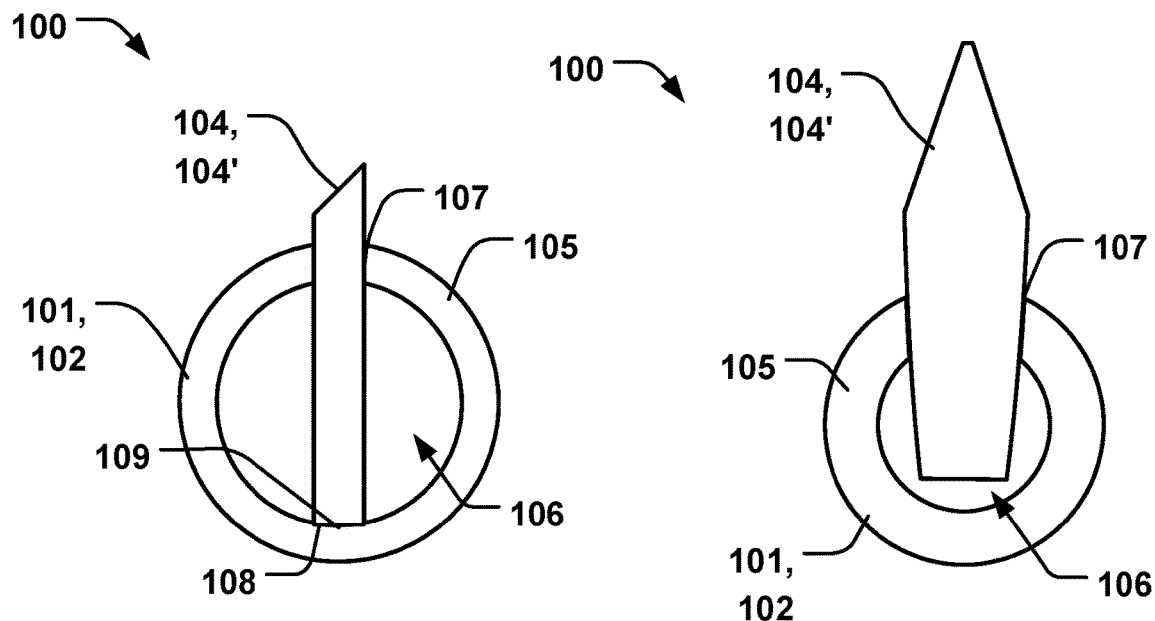
Fig. 7a
Fig. 7b

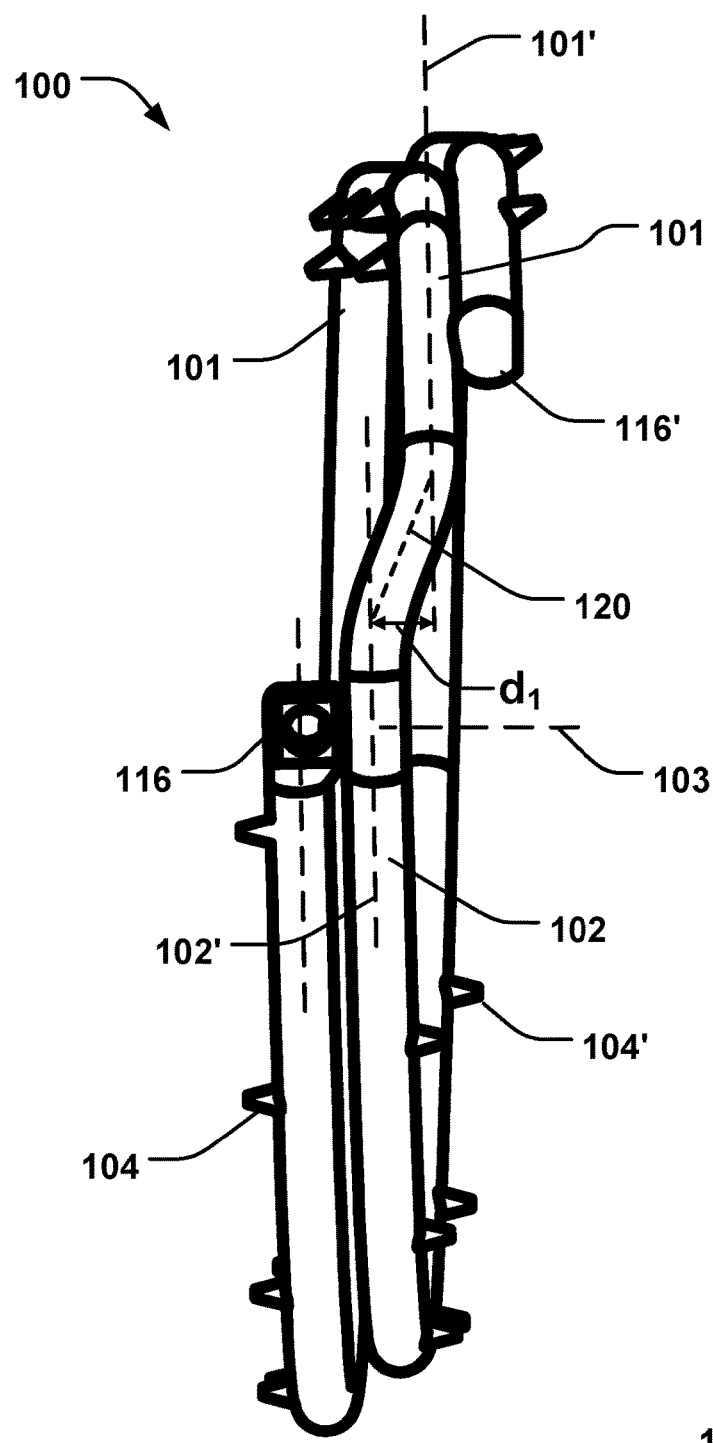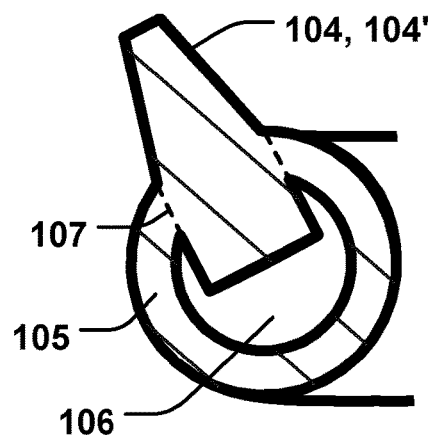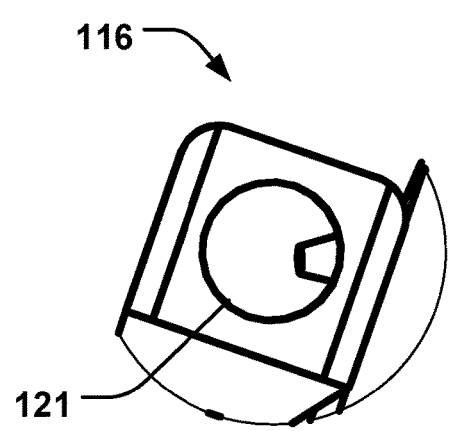
Fig. 12  Fig. 13

A' - A'

B' - B'

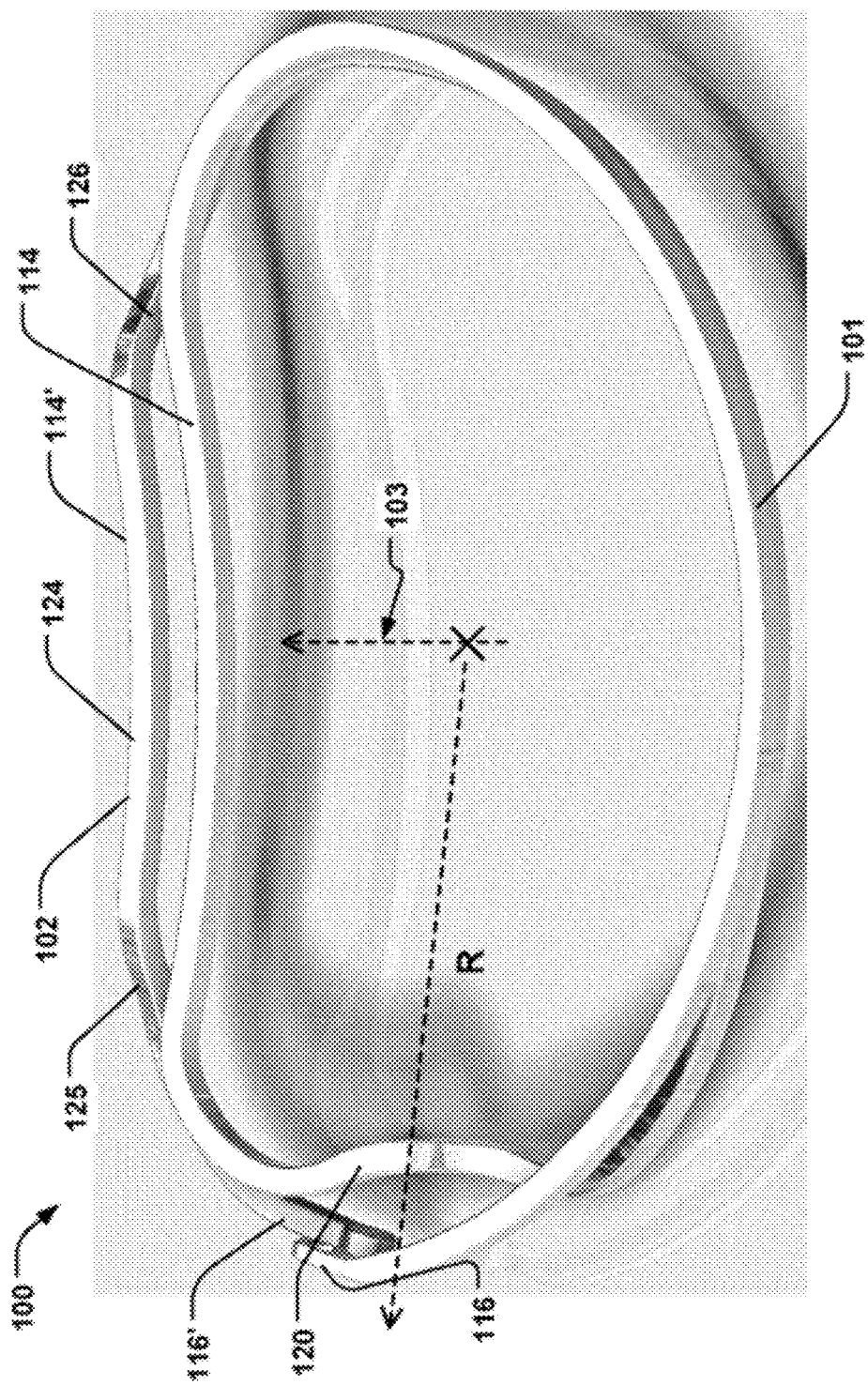

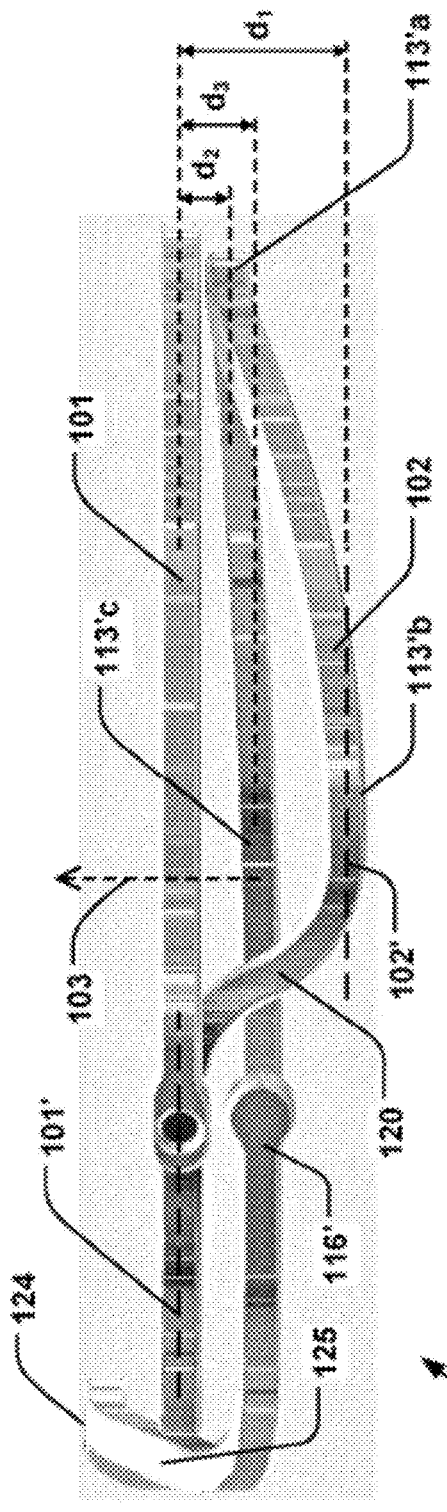
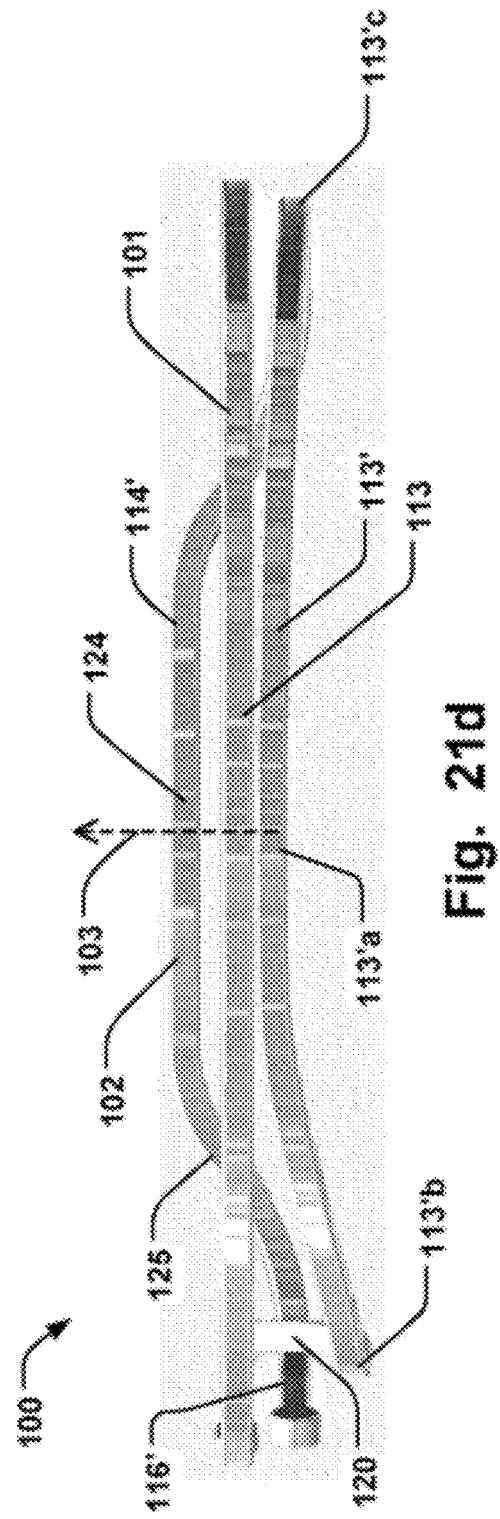

ANNULOPLASTY DEVICE

FIELD OF THE INVENTION

This invention pertains in general to the field of cardiac valve repair. More particularly the invention relates to an annuloplasty device, such as an annuloplasty ring or helix, for positioning at the heart valve annulus and a method of repairing a defective heart valve.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. The annuloplasty ring is typically implanted around the annulus of the heart valve.

A problem with prior art annuloplasty implants is to achieve correct positioning at the heart valve and fixate the implant in the correct position. Suturing devices for annuloplasty implants have disadvantages that makes it difficult to suture in the correct position, thereby resulting insufficient suturing strength, and also in a very time-consuming procedure, which increases the risks for the patient. Furthermore, suturing devices are often not sufficiently compact for catheter based procedures. The use of clips for positioning annuloplasty implants is also associated with challenges, in particular when implanting helix rings that are to be positioned on either side of a heart valve. Insufficient fixation of such implant lead to traumatic effects since the fixation structure must ensure the correct position of the device over time. A further problem in the prior art is thus also to achieve a reliable fixation at the annulus of the heart valve. An annuloplasty implant is intended to function for years and years, so it is critical with long term stability in this regard.

The above problems may have dire consequences for the patient and the health care system. Patient risk is increased.

Hence, an improved annuloplasty implant or device would be advantageous and in particular allowing for avoiding more of the above mentioned problems and compromises, and in particular ensuring secure fixation of the annuloplasty device, during the implantation phase, and for long-term functioning, in addition to a less complex procedure, and increased patient safety. A related method would also be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect an annuloplasty device is provided comprising first and second support rings having a coiled configuration in which the first and second support rings are arranged as a coil around a central axis, wherein the first and second support rings are configured to be arranged on opposite sides of native heart valve leaflets of a heart valve, the first support ring transitions to the second support ring over a transition section, wherein the transition section is adapted to be arranged at a commissure of the heart valve leaflets, the first and second support rings extend in respective first and second coil planes being essentially perpendicular to the central axis, the transition section bends at least partly along the central axis so that the first coil plane is separated a distance ($d_1$) from the second coil plane along the central axis at the transition section.

According to a second aspect a method of repairing a defective heart valve is provided, comprising positioning a second support ring of an annuloplasty device on a ventricular side of the heart valve, and positioning a first support ring of the annuloplasty device on an atrial side of the heart valve, the first and second support rings are arranged as a coil around a central axis on opposite sides of native heart valve leaflets of the heart valve. The first and second support rings are positioned so that the first support ring transitions to the second support ring over a transition section positioned at a commissure of the heart valve leaflets. The first and second support rings extend in respective first and second coil planes being essentially perpendicular to the central axis. The transition section bends at least partly along the central axis so that the first coil plane is separated a distance from the second coil plane along the central axis at the transition section.

Further examples of the invention are defined in the dependent claims, wherein features for the first aspect may be implemented for the second and subsequent aspects and vice versa.

Some examples of the disclosure provide for a facilitated positioning of an annuloplasty device at a heart valve.

Some examples of the disclosure provide for a facilitated fixation of an annuloplasty device at a heart valve.

Some examples of the disclosure provide for a less time-consuming fixation of an annuloplasty to a target site.

Some examples of the disclosure provide for securing long-term functioning and position of an annuloplasty device.

Some examples of the disclosure provide for a reduced risk of damaging the anatomy of the heart such as the annulus or the valve leaflets.

Some examples of the disclosure provide for a more secure implantation of an annuloplasty device in narrow anatomies.

Some examples of the disclosure provide for an annuloplasty device with improved accommodation to the anatomy of a heart valve.

Some examples of the disclosure provide for an annuloplasty device with an increased retention force at the heart valve.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 6 is a schematic illustration of an annuloplasty device, in a perspective view, according to an example of the disclosure;

FIGS. 7a-b are schematic illustrations of a cross-section of a first or second support ring of an annuloplasty device, with an attached retention unit, according to examples of the disclosure;

FIG. 11c is a schematic illustration of a detail of an annuloplasty device, with an enlarged view of the detail in FIG. 11a, according to an example of the disclosure;

FIG. 12 is a schematic illustration of an annuloplasty device, in a side view of FIG. 10 along the vertical direction Y, according to an example of the disclosure;

FIG. 13 is a schematic illustration of a detail of an annuloplasty device, from the view in FIG. 12, according to an example of the disclosure;

FIGS. 20a-c are schematic illustrations of an annuloplasty device, in perspective views, according to examples of the disclosure; and FIGS. 21a-d are side views of the annuloplasty device in FIGS. 20a-c, according to examples of the disclosure.

DESCRIPTION OF EMBODIMENTS

Figure 1A:
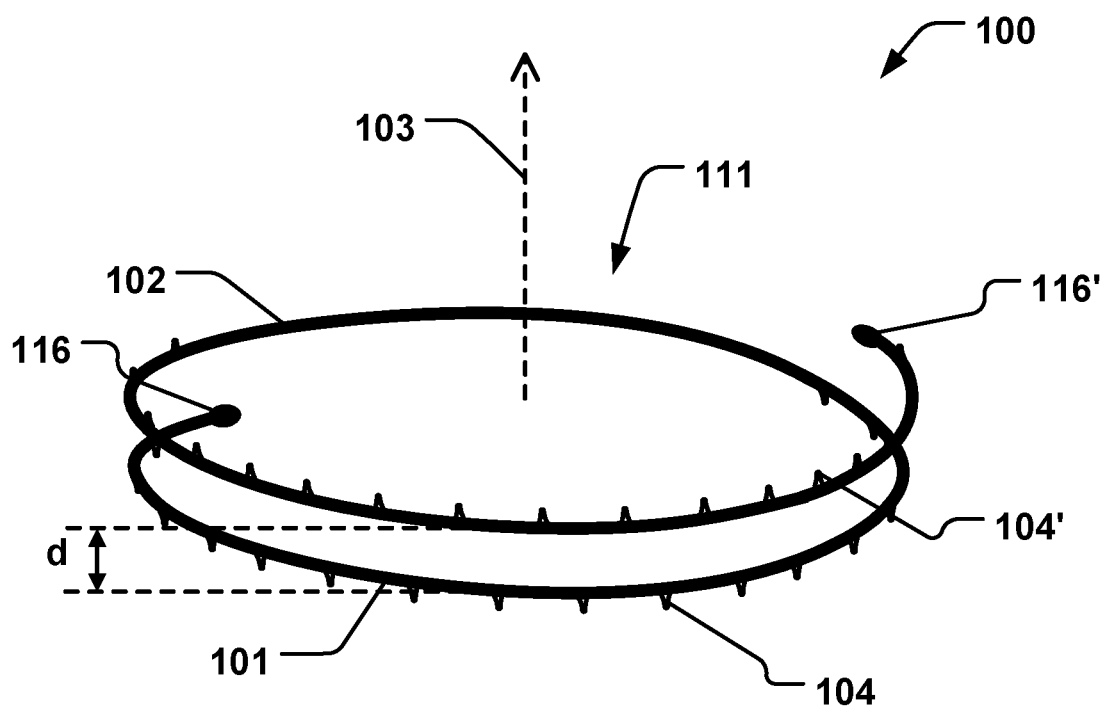
FIG. 1a is a schematic illustration of an annuloplasty device, in a perspective view, where the first and second support rings are in a relaxed first state, according to an example of the disclosure.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 3:
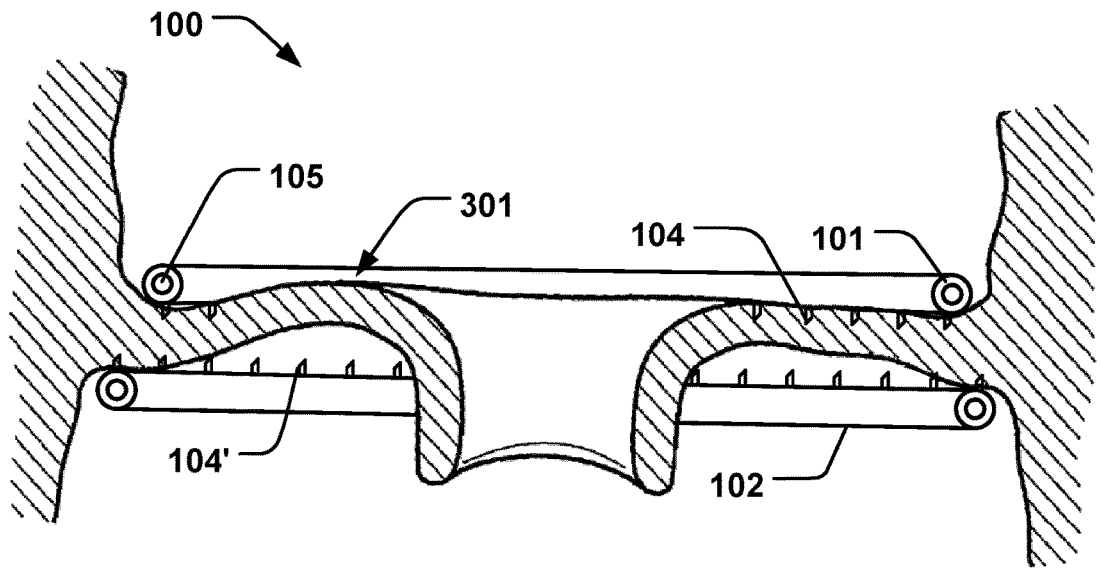
FIG. 3 is a schematic illustration of an annuloplasty device, in a side view, where the annuloplasty device is positioned above and below valve leaflets, according to an example of the disclosure.
Figure 4:
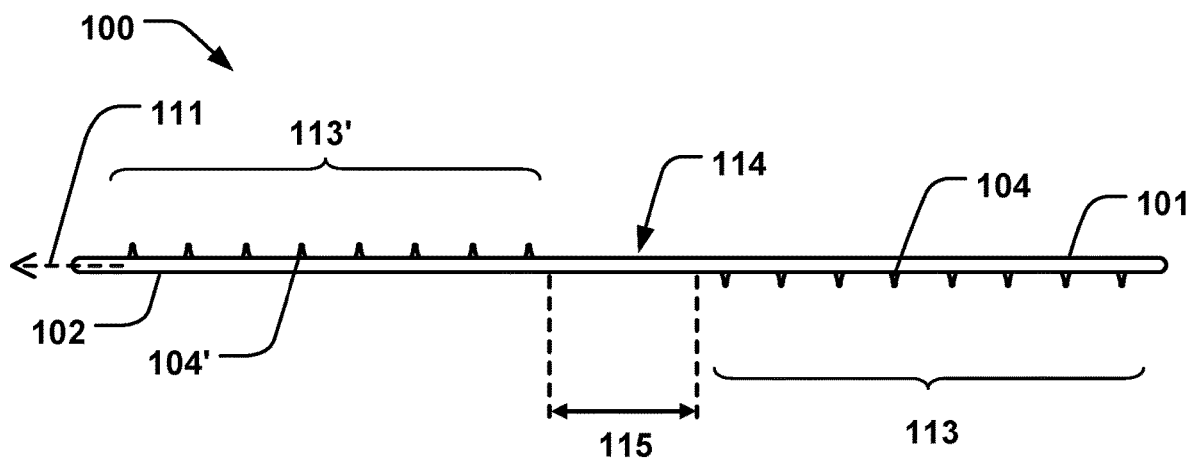
FIG. 4 is a schematic illustration of an annuloplasty device, in a side view, where the annuloplasty device is in a stretched configuration, according to an example of the disclosure.
Figure 5A:
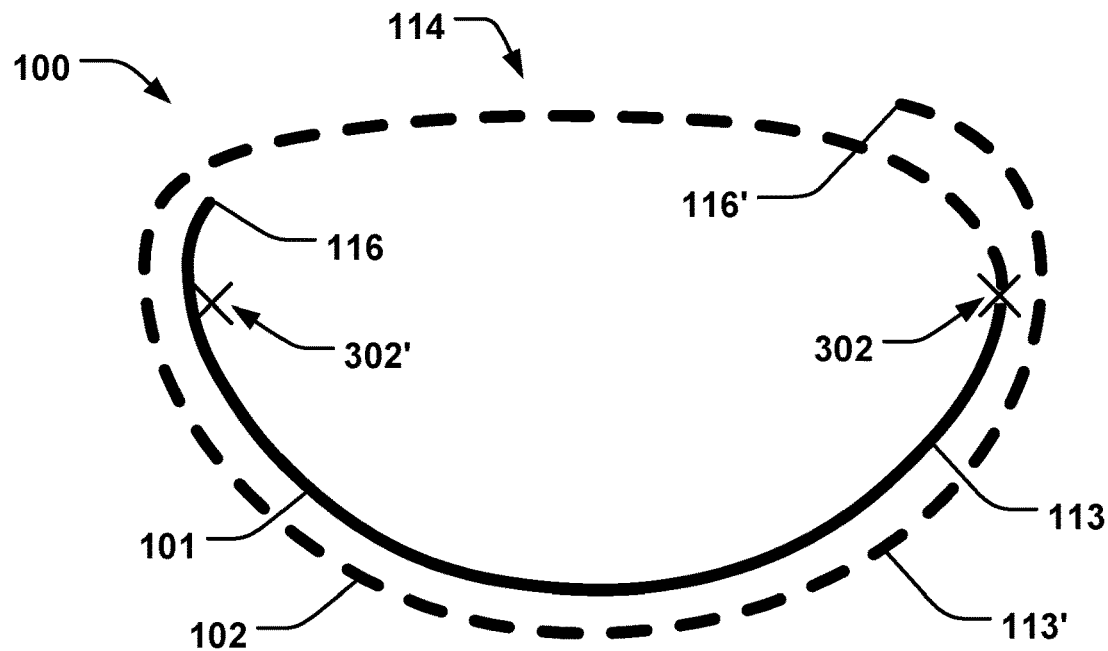
FIGS. 5a-b are schematic illustrations of an annuloplasty device, in a top-down view, according to examples of the disclosure.
Figure 5B:
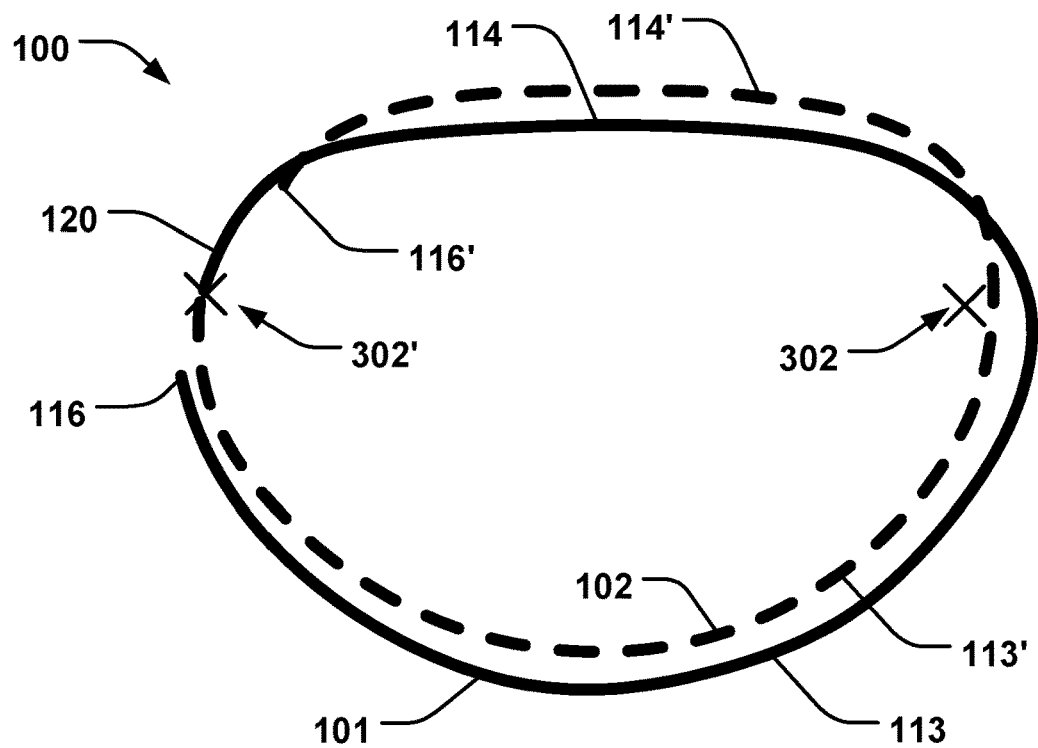

FIG. 1 schematically illustrates an example of an annuloplasty device 100 comprising a first support ring 101 and second support ring 102 which are adapted to be arranged as a coil, i.e. in a helix-shape, in a coiled configuration around a central axis 103, as illustrated in FIG. 1a. The device 100 is arranged in the coiled configuration at least when in a relaxed state of the material from which the device 100 is formed, i.e. free from outside forces acting upon the device 100. The coil-shaped device 100 has two free ends 116, 116'. The first and second support rings 101, 102, and the respective free ends 116, 116', are configured to be arranged on opposite sides of native heart valve leaflets 301 of a heart valve, as illustrated in e.g. the side view of FIG. 3. As shown in FIG. 3, the first support ring 101 may be arranged on an atrial side of the heart valve, and the second support ring 102 may be arranged on a ventricular side (the second support ring 102 is also shown with dashed lines in the top-down views of FIGS. 5a-b, where the valve leaflets have been omitted). The second support ring 102 is illustrated with a dashed line and is in these examples arranged on the ventricular side of the heart valve, whereas the first support ring 101 is arranged on the atrial side of the heart valve (shown with solid line). The first support ring 101 may thus extend along the annulus of the heart valve on the atrial side. The first and second support rings 101, 102, are connected to form a coil- or helix shaped ring, as an integral continuous ring. The coil extends through the valve opening at a commissure 302, 302', thereof, as schematically illustrated in FIGS. 5a-b. The first and second support rings 101, 102, may thus assume the coiled configuration also when in an implanted state. As explained further below, the device 100 may comprise a shape-memory material, so that the device 100 re-assumes the coiled configuration after having been delivered from a catheter (not shown) to the target site, after having been temporarily restrained in an elongated configuration of the catheter. FIG. 4 is a schematic illustration of the annuloplasty device 100 when in such elongated stretched state. The annuloplasty device 100, i.e. annuloplasty implant 100, may comprise a shape memory material, such as NiTiNol, or another suitable biocompatible alloy that can be heat-set in defined shapes, i.e. in a defined relaxed shape in absence of outside acting forces, as described further below, in a heat treatment procedure. The annuloplasty device 100 may pinch the tissue of the valve leaflets 301, between the first and second support rings 101, 102, i.e. with forces acting parallel with the central axis 103.

Figure 1B:
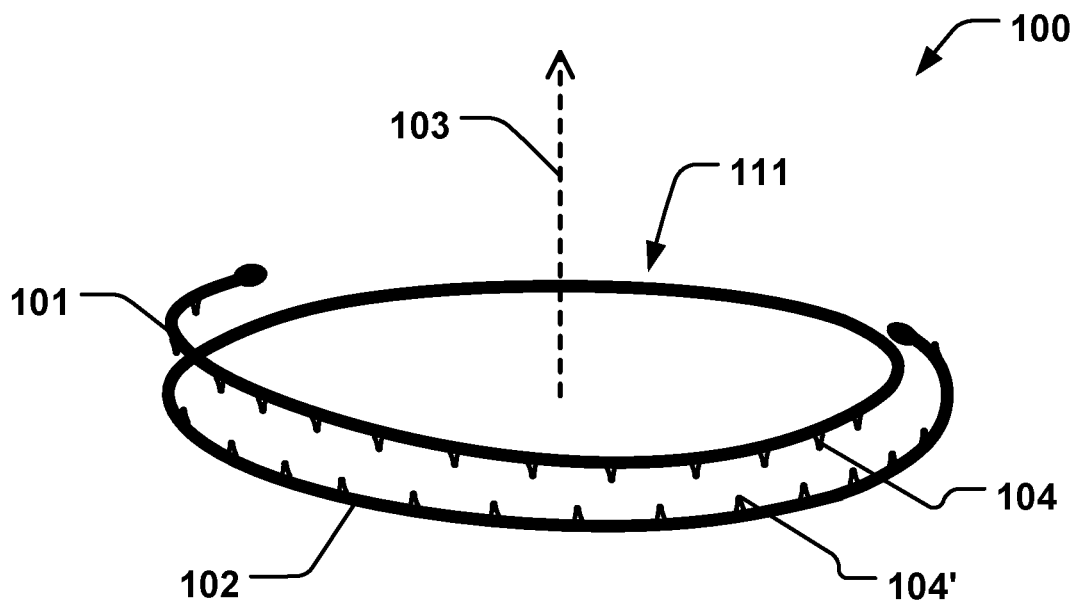
FIG. 1b is a schematic illustration of an annuloplasty device, in a perspective view, where the first and second support rings are in a displaced second state, according to an example of the disclosure.
Figure 2A:
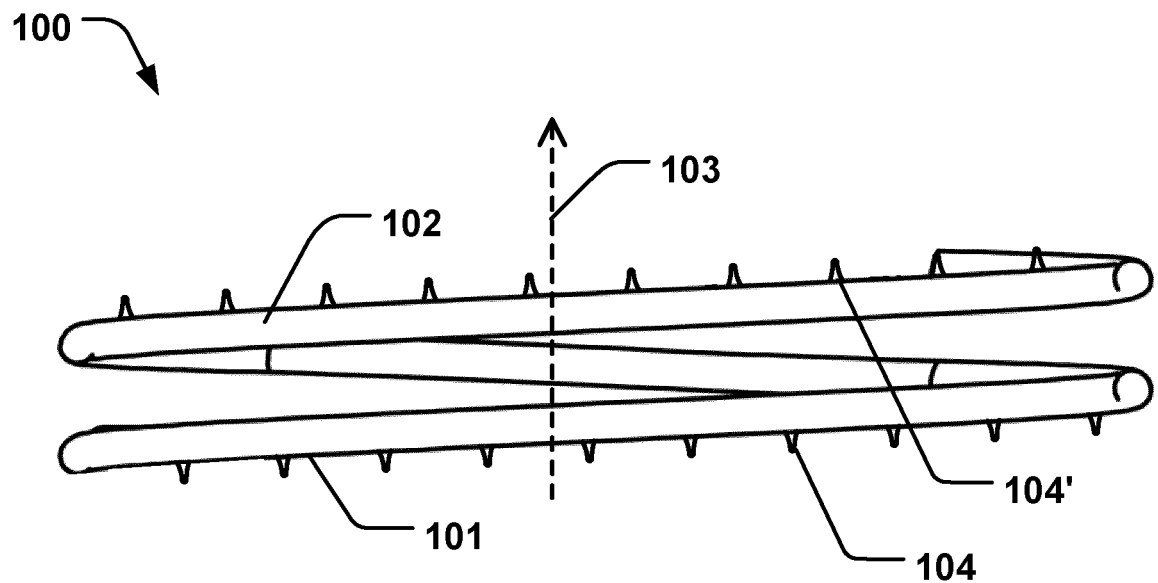
FIG. 2a is a schematic illustration of an annuloplasty device, in a side view, where the first and second support rings are in a relaxed first state, according to an example of the disclosure.
Figure 2B:
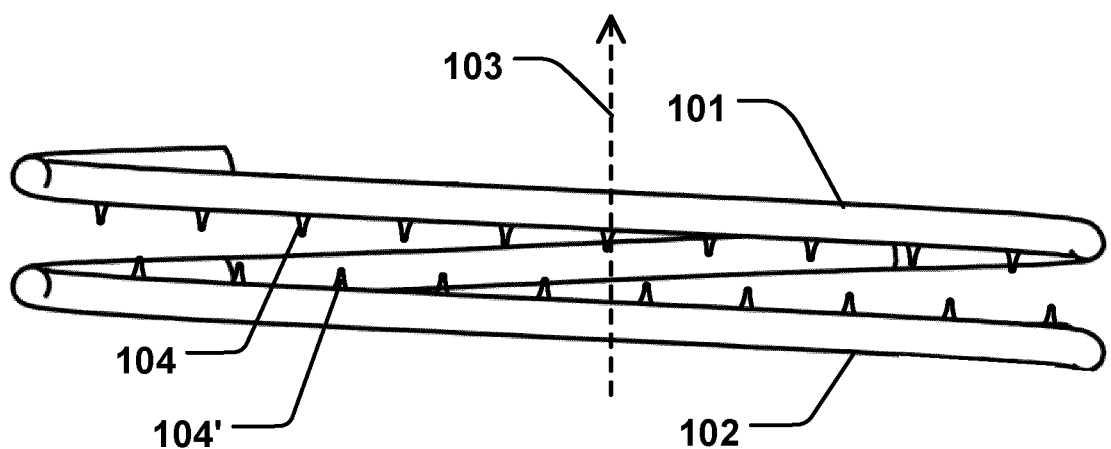
FIG. 2b is a schematic illustration of an annuloplasty device, in a side view, where the first and second support rings are in a displaced second state, according to an example of the disclosure.
Figure 16:
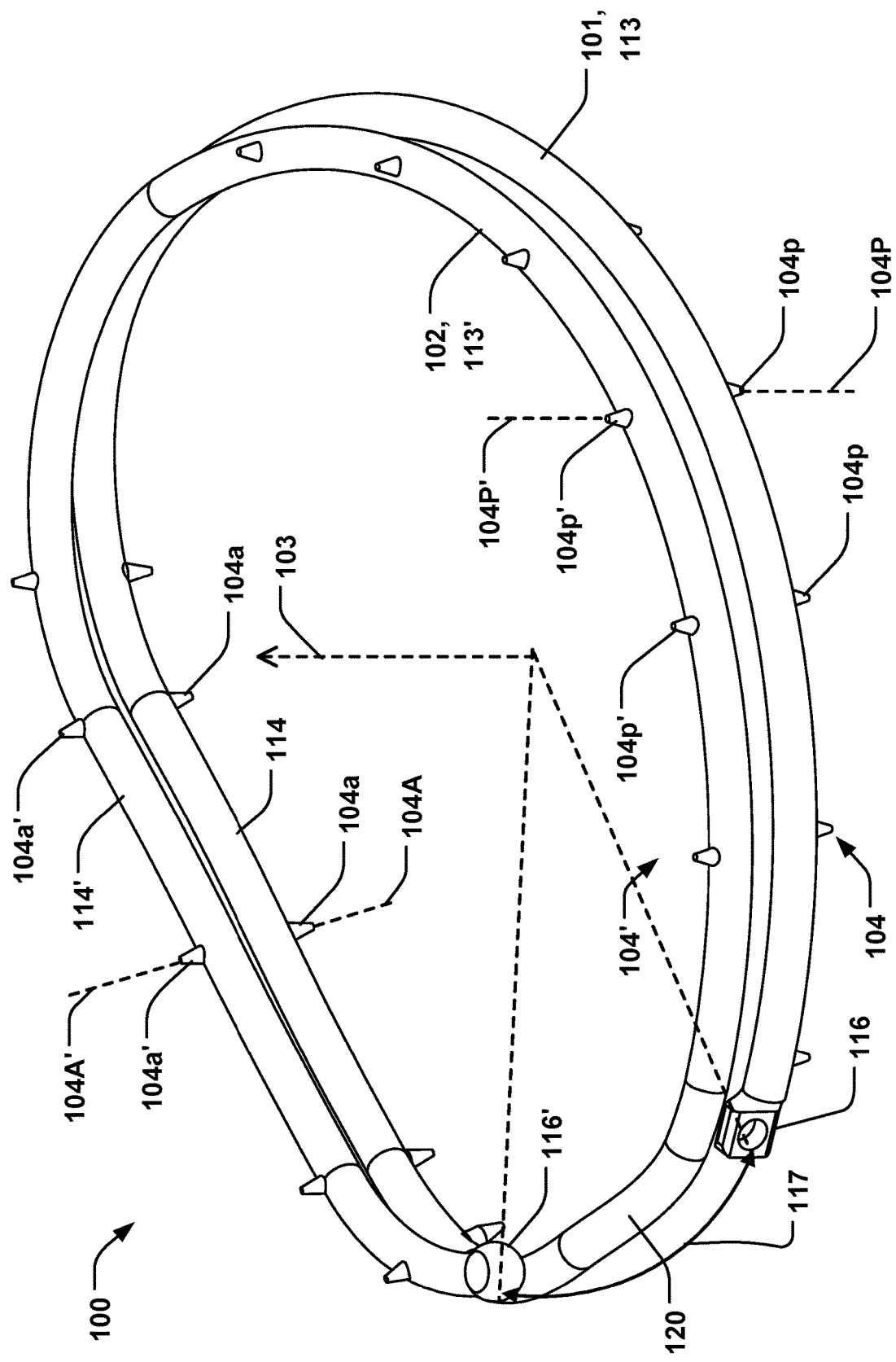
FIG. 16 is a schematic illustration of an annuloplasty device, in a perspective view, according to an example of the disclosure.

The annuloplasty device 100 may optionally comprise retention units 104, 104', as schematically illustrated in the perspective views of e.g. FIGS. 1a-b, 16, and side views of FIGS. 2-4, 12, 14, 19a-b and cross-sectional views of FIGS. 7a-b (i.e. looking along the longitudinal direction 111 in which the first and second rings 101, 102, extend), and FIGS. 11a-b, 18a-b. FIGS. 1a-b show examples where a plurality of retention units 104, 104', are arranged on the first and second support rings 101, 102. The example in FIG. 4 show the device 100 in an elongated stretched configuration, e.g. as arranged while being restrained in a catheter. However, as mentioned above, the device 100 assumes the coiled shape when released from the catheter, whereupon the retention units 104, 104', may engage the tissue on the atrial and ventricular sides of the heart valve, as exemplified in FIG. 3 and as described further below. The retention units 104, 104', are configured to engage the tissue of the valve and anchor the device 100 at the valve. The first support ring 101 may comprise first retention units 104, and the second support ring 102 may comprise second retention units 104'.

The first support ring 101 transitions to the second support ring 102 over a transition section 120, as illustrated in e.g. FIGS. 12, 16, 19a, 20a-c, 21a-d. The transition section 120 is adapted to be arranged at a commissure 302, 302', of the heart valve leaflets, e.g. at a commissure 302' as illustrated in FIG. 5b. The first and second support rings 101, 102, extend in respective first and second coil planes 101', 102', being essentially perpendicular to the central axis 103. The transition section 120 may bend at least partly along the central axis 103 so that the first coil plane 101' is separated a distance ($d_1$) from the second coil plane 102' along the central axis 102 (i.e. along a direction parallel to the central axis) at the transition section 120. Having such transition section 120 where the coil planes 101', 102', are locally displaced a distance ($d_1$), and at a position corresponding to the location of the commissure 302, 302', provides for improved accommodation of the first and second support rings 101, 102, to the anatomy at the opposite sides of the valve, in particular as the heart beats. Having a step-down in the coil planes 101', 102', or an "S-shape", or "Z-shape", of the support rings 101, 102, at the transition section 120 due to separation distance ($d_1$) provides for a better coaptation of the first and second support rings 101, 102, at the commissure 302, 302'. I.e. the risk of having the moving valve leaflets pulling on any of the support rings 101, 102, at the commissure 302, 302', is minimized because the first coil plane 101' of the first support ring 101 on the atrial side transitions to the second coil plane 102' of the second support ring 102 over a reduced distance at the transition section 120 due to the displacement ($d_1$) (i.e. a local section 120 of increased pitch or rise of the coil formed by the adjacent support rings 101, 102). This means that the first and second support rings 101, 102, may conform better to the two opposite sides of the valve close to the commissure 302, 302'. The annuloplasty device 100 may thus be secured at the valve in a safer manner, while the risk of dislocations is minimized. The position of the transition section 120 may be varied depending on which commissure 302, 302', the first/second support rings 101, 102, extend through the valve leaflets. The transition section 120 may thus have an increased slope or pitch relative the central axis 103 compared to the remaining portions of the first and second support rings 101, 102.

Figure 17A:
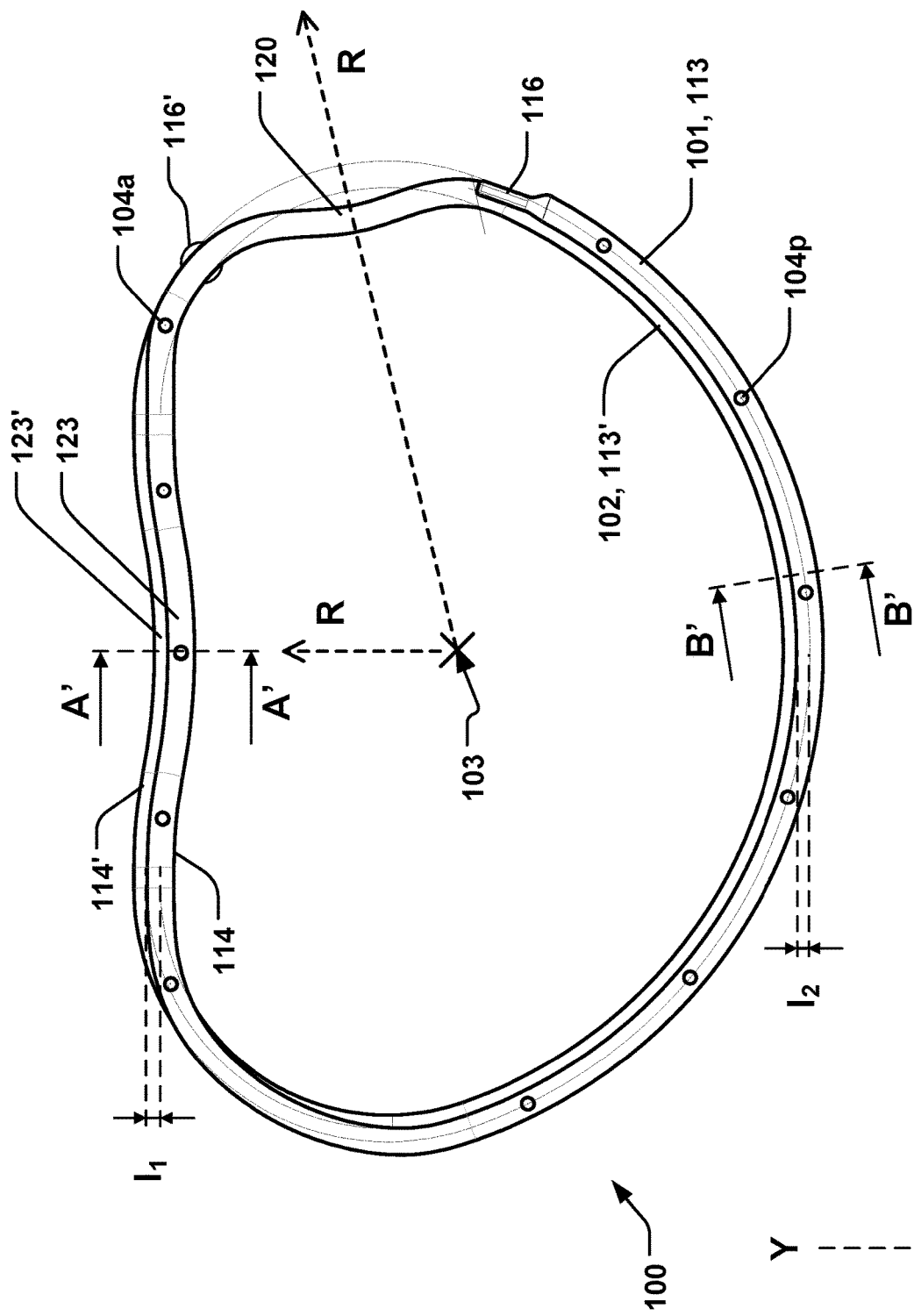
FIG. 17a is a schematic illustration of an annuloplasty device, in a top-down view, according to an example of the disclosure.
Figure 19A:
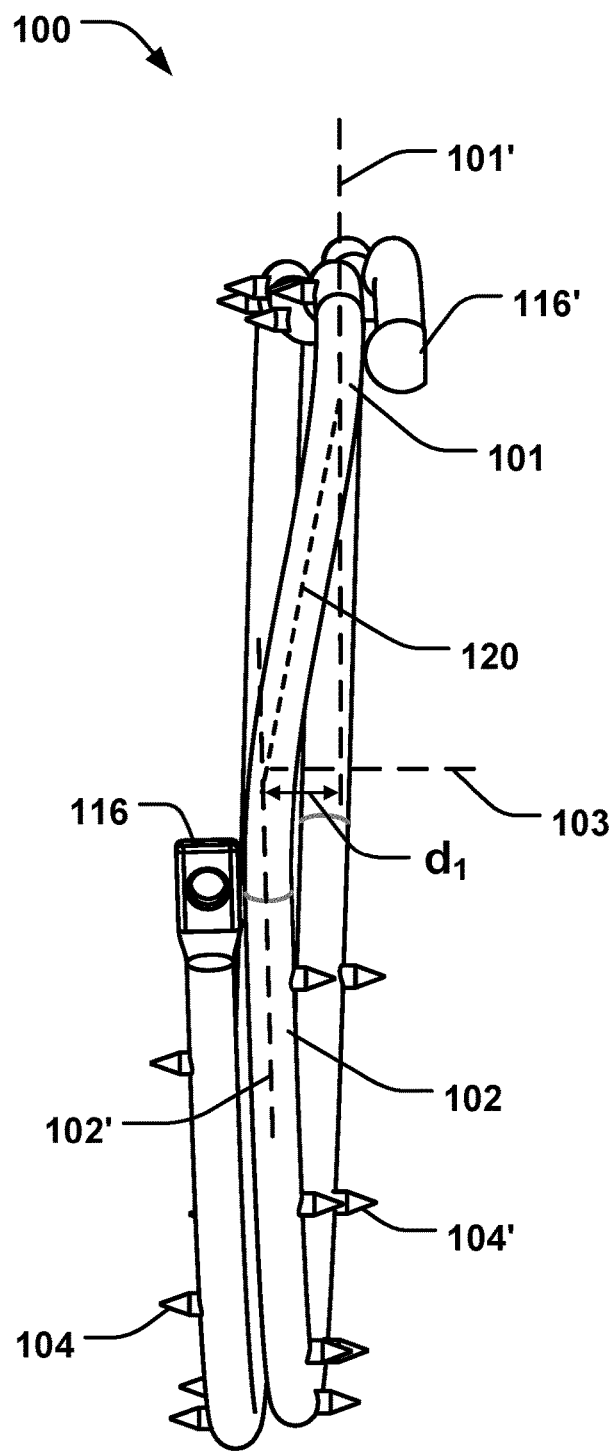
FIG. 19a is a schematic illustration of an annuloplasty device, in a side view of FIG. 17a along the vertical direction Y, according to an example of the disclosure.
Figure 19B:
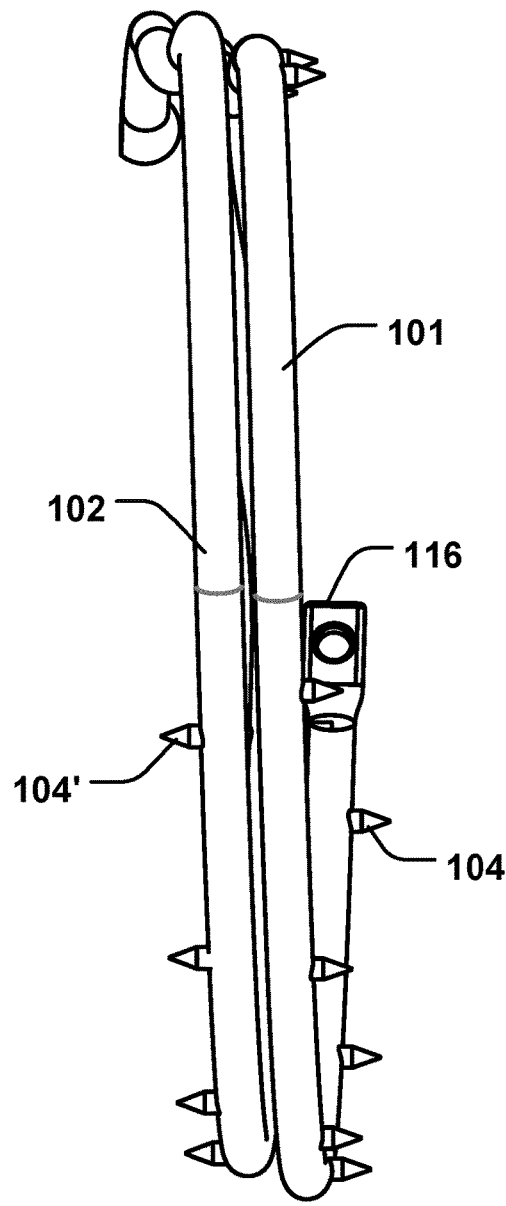
FIG. 19b is a schematic illustration of an annuloplasty device, in a side view of FIG. 17a along the vertical direction Y, and from an opposite side compared to FIG. 19a, according to an example of the disclosure.

The length of the transition section 120 may in one example correspond to approximately an off-set distance 117 between free ends 116, 116', as schematically illustrated in FIGS. 16, 17a, 19a. In one example the transition section 120 may be arranged after the first support ring 101 forms essentially one complete loop, as exemplified in FIG. 20c.

Figure 17B:
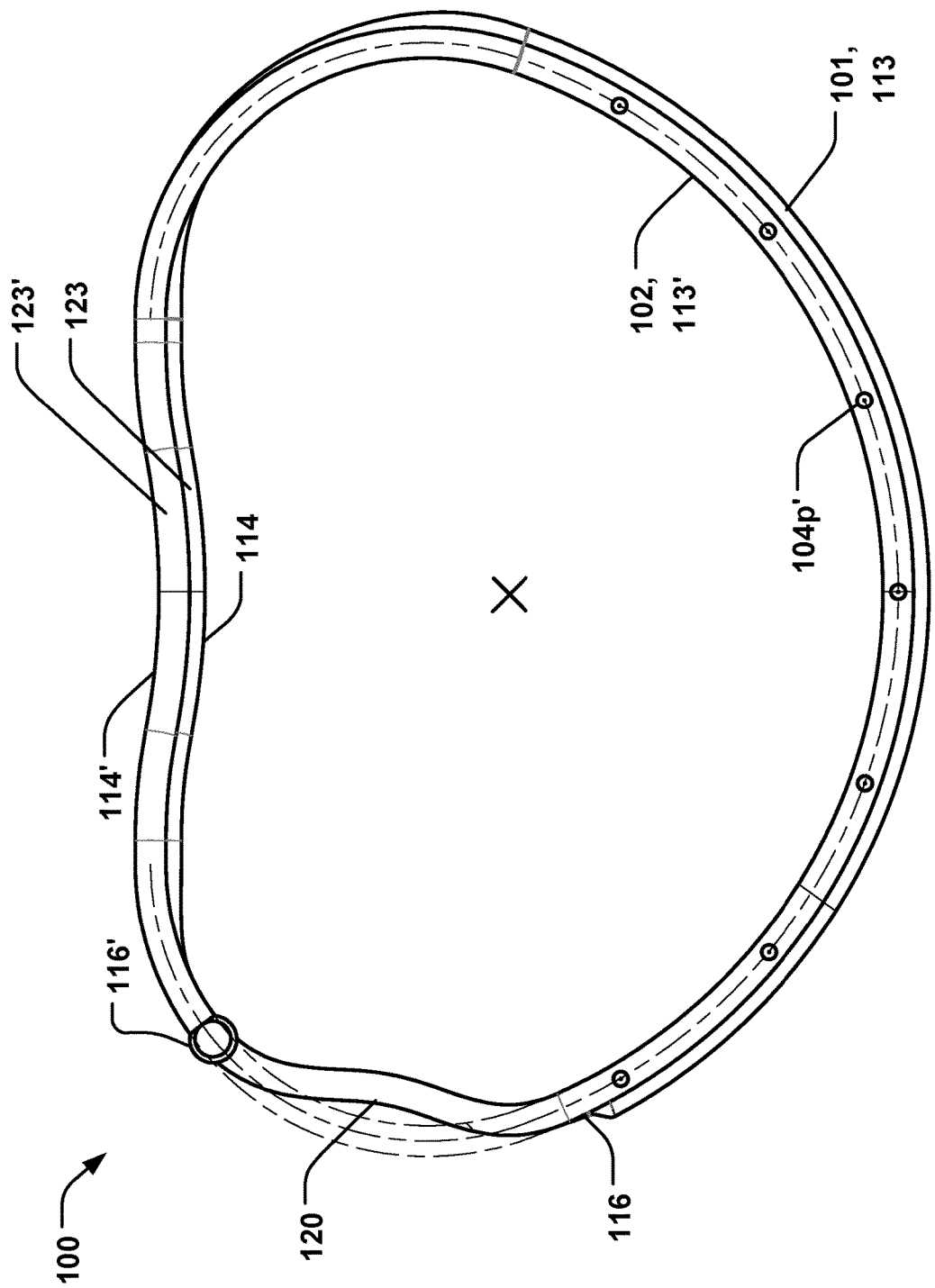
FIG. 17b is a schematic illustration of an annuloplasty device, in a top-down view and from an opposite side of the annuloplasty device of the view in FIG. 17a, according to an example of the disclosure.

The transition section 120 may bend at least partly along a radial direction (R), where the radial direction (R) is perpendicular to the central axis 103, so that the transition section 120 is concave towards the radial direction (R). FIGS. 17a-b and 20b illustrate examples of such concave bend, or "C-curve", of the transition section 120 towards the radial direction (R). This provides for further improving the coaptation of the first and second support rings 101, 102, to the valve anatomy close to the commissure 302, 302'. The risk of having a disadvantageous force transfer or friction between the moving valve leaflets and any of the support rings 101, 102, at the commissure 302, 302', is minimized. The first and second support rings 101, 102, may extend along the annulus as far as possible while extending through the commissure 302, 302', with minimized impact on the valve motion, as the concave bend of the transition section 120 allows for adapting to anatomies where the commissure 302, 302', is located closer to the central axis 103 than the annulus. The annuloplasty device 100 may thus be secured at the valve in a further improved manner, while the risk of dislocations in the long term is minimized.

The advantageous features of having a transition section 120, as described in relation to e.g. FIGS. 12, 16, 17a-b, 19a, 20a-c, 21a-d, above provide for an improved annuloplasty device 100 with an improved anchoring into the tissue, also in absence of the below discussed displacement (d) in the relaxed state (FIGS. 1a-b). In absence of the displacement (d) in the relaxed state, the annuloplasty device 100 has a relaxed state corresponding to the illustration in FIG. 1b. In case the annuloplasty device 100 comprises retention units 104, 104', the retention units 104, 104', point in a direction towards each other in the relaxed state, in absence of the below discussed displacement (d) in the relaxed state. The transition section 120 as described throughout the disclosure thus provides for a separate aspect of the invention.

The first support ring 101 may comprise a first posterior bow 113 and a first anterior portion 114. The second support ring 101 may comprise a second posterior bow 113' and a second anterior portion 114'. The first and second posterior bows 113, 113', may be adapted to conform to a posterior aspect of the heart valve, i.e. along the posterior leaflet, having a bow-shaped extension. The first and second anterior portions 114, 114', may each have a straighter extension or at least an extension which is less bent than the bow-shaped posterior sides 113, 113'. This is exemplified in e.g. FIGS. 5b, 9, 10, 16, 17a, 20a-c. The first and second anterior portions 114, 114', may thus be adapted to conform to an anterior aspect of the heart valve, i.e. along an anterior leaflet.

Figure 20A:
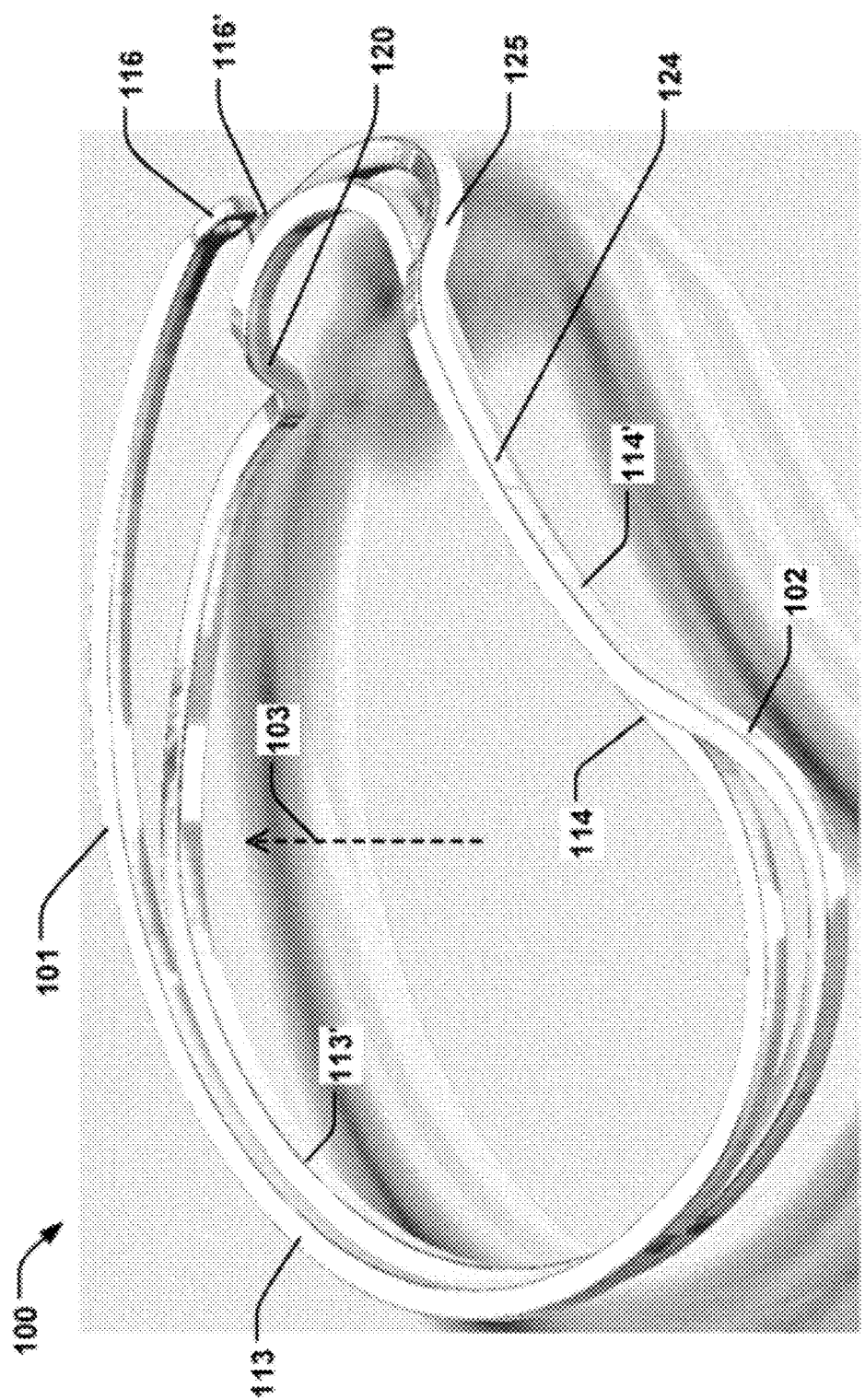
Figure 20C:
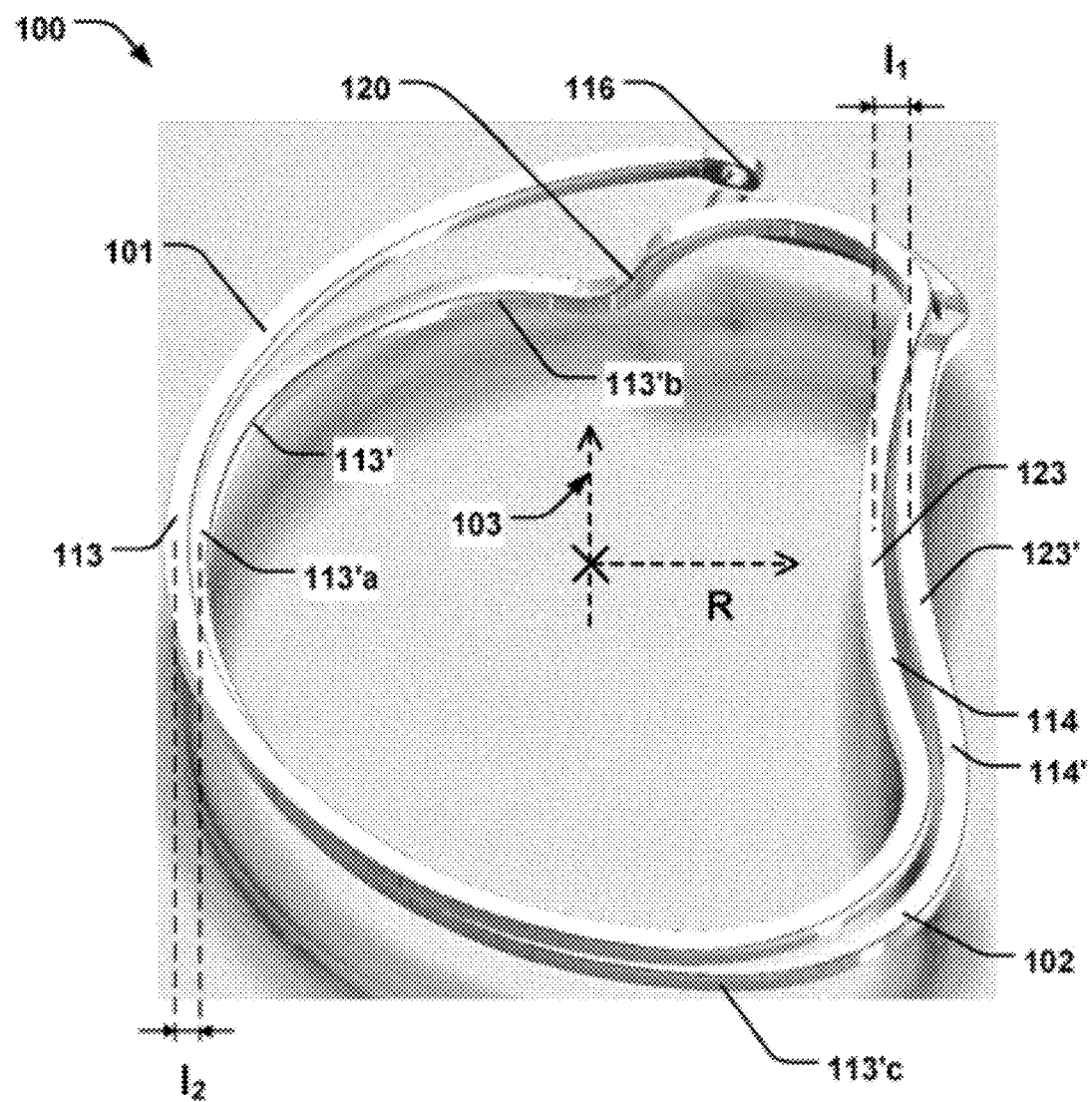
Figure 21A:
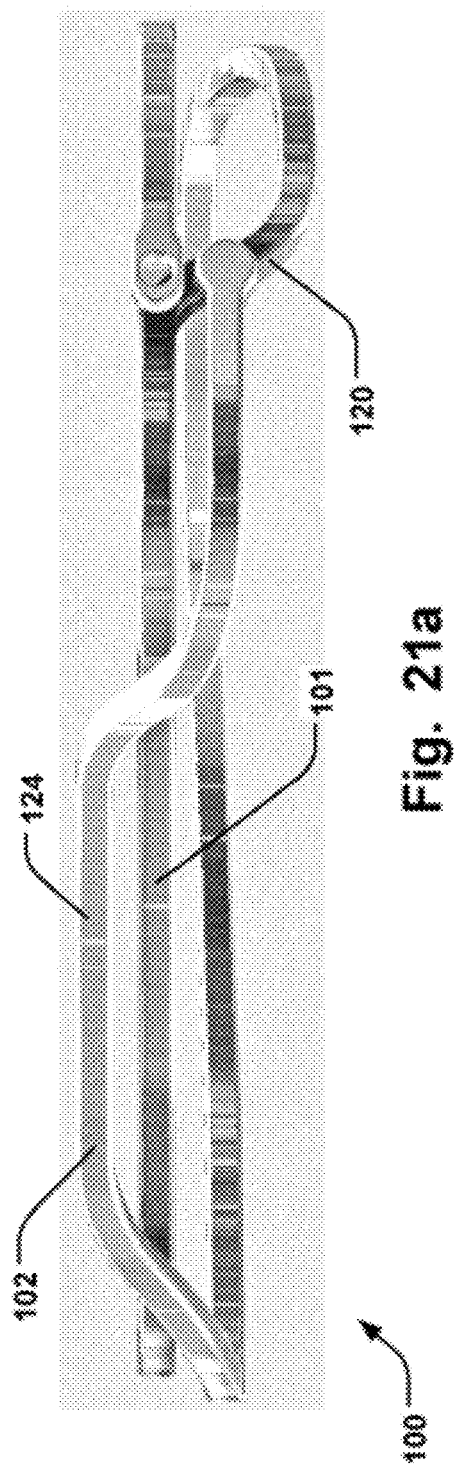
Figure 21B:
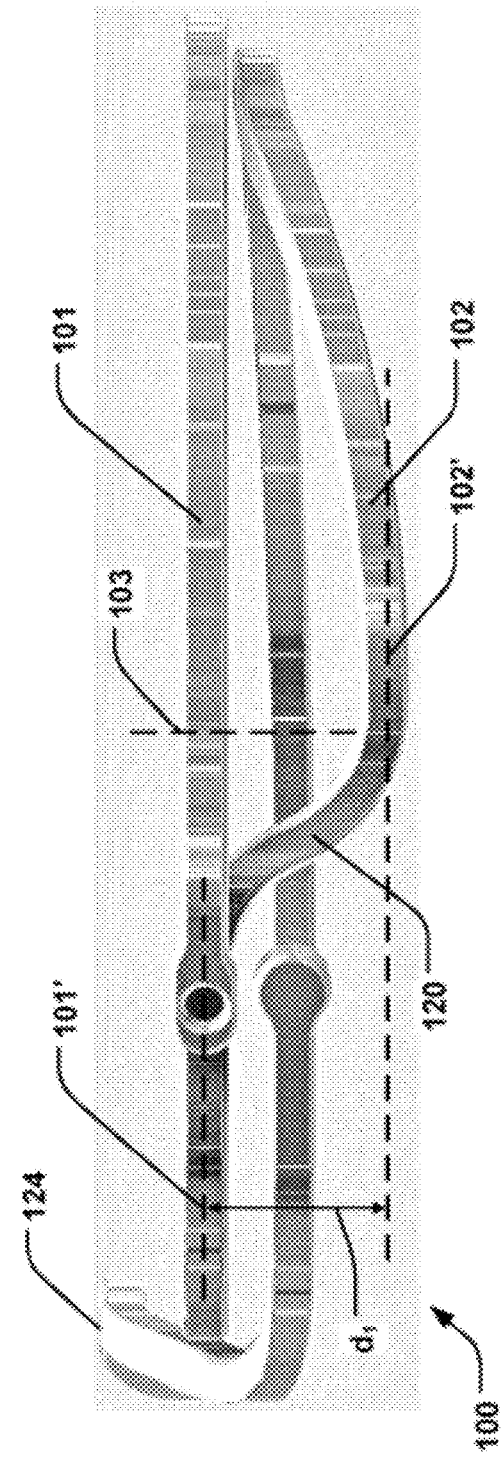

At least part of the first anterior portion 114 and/or the second anterior portion 114' may be curved to form a respective concave section 123, 123', being concave towards a radial direction (R), where the radial direction (R) is perpendicular to the central axis 103, as schematically illustrated e.g. in FIGS. 17a and 20c. This provides for further improving the accommodation of the first and second support rings 101,102, to the anatomy of the valve and its annulus. A more secure attachment of the annuloplasty device 100 is achieved, and long-term reliability of the implantation, since interference with the natural heart valve movements can be minimized.

The first anterior portion 114 may be displaced a distance ($I_1$) from the second anterior portion 114' along a radial direction (R) so that at least part of the second anterior portion 114' extends with a greater radius (r) from the central axis 103 than the first anterior portion 114, as schematically illustrated in e.g. FIGS. 9, 11a, 17a, 18a, 20c. Thus, when the first support ring 101 is arranged on the atrial side and the second support ring 102 is arranged on the ventricular side, the second anterior portion 114' of the second support ring 102 will extend with a greater radius from the central axis 103 than the first anterior portion 114 of the first support ring 101. This is also exemplified in FIG. 3. Having a greater radius of the second support ring 102 on the ventricular side provides for an effective pinching of the valve tissue at the aorto-septal wall, and thus a more secure anchoring of the annuloplasty device 100.

As schematically illustrated in e.g. FIGS. 9, 11b, 17a, 18b, 20c, the first posterior bow 113 may be displaced a distance ($I_2$) from the second posterior bow 113' along a radial direction (R). The radial direction (R) is perpendicular to the central axis 103. The off-set between the first and second posterior bows 113, 113', provides for an improved fixation of the annuloplasty device 100 on a downsized posterior annulus and thus a more effective anchoring of the annuloplasty device 100. At least part of the first posterior bow 113 may thus extend with a greater radius (r) from the central axis 103 than the second posterior bow 113', as schematically illustrated in e.g. FIGS. 9, 11b, 17a, 18b, 20c. Axis 103' in FIGS. 11a-b, 18a-b, is parallel with the central axis 103. Having the first support ring 101 extending with a greater radius in the radial direction along the posterior bow 113 on the atrial side compared to the posterior bow 113' of the second support ring 102 on the ventricular side provides for an improved coaptation to the anatomy around the valve on the ventricular side, and thus a more secure anchoring of the annuloplasty device 100 and less interference with the native leaflets and chordae. Circumflexing of the chordae may also be facilitated in this case.

In another example however it should be understood that at least part of the second posterior bow 113' may extend with a greater radius (r) from the central axis 103 than the first posterior bow 113.

The advantageous features of having displacement distances ($I_1$, $I_2$), as described in relation to FIGS. 9, 11, 17, 18, 20c provides for an improved annuloplasty device 100 with an improved anchoring into the tissue, also in absence of below discussed displacement (d) in the relaxed state (FIGS. 1a-b). I.e., in absence of the displacement (d) in the relaxed state, the annuloplasty device 100 has a relaxed state corresponding to the illustration in FIG. 1b. The displacement distances ($I_1$, $I_2$) thus also provides for a separate aspect of the invention.

The first and second support rings 101, 102, may have a separation distance (d) and may be movable relative each other along the central axis 103 so that the separation distance (d) is variable. In one example, the first and second support rings 101, 102, comprises a resilient shape-memory material and may be movable along the central axis 103 from a relaxed first state, as illustrated in FIG. 1a, to a displaced second state, as illustrated in FIG. 1b. The first state may thus correspond to the defined heat-set shape of the material from which the first and second support rings are formed. In the second state the first and second rings have been forced to a displaced position where the first and second rings have shifted their relative positions along the axial direction 103 (FIG. 1b). There may thus a resilient bias from the second state towards the first state. Thus, the first and second support rings 101, 102, strive to assume the first state when displaced to the second state to pinch the valve leaflets from the opposite sides. In FIG. 1b, the first support ring 101 will strive to move towards the second support ring 102, and vice versa, since in the heat set relaxed shape in FIG. 1a, the first and second support rings 101, 102, have an inverted relative position with the first support ring 101 below the second support ring 102. If the force acting upon the first and second support rings 101, 102, is removed the latter will thus move towards each other and past each other so that the inverted relative position in FIG. 1a is assumed. Having the inverted arrangement of the first and second support rings 101, 102, in the relaxed shape as described above provides for an increased compression force on the valve tissue when the first and second rings 101, 102, are arranged in the second state at opposite sides of the valve leaflets, as further seen in FIG. 3. The increased compression force provides for a more secure, robust, and reliable anchoring of the annuloplasty device at the heart valve. This provides for an improved function and safety for the patient, both short term and long term. The implantation procedure may thus be accomplished in less time and with improved control. A secure positioning of the first and second support rings 101, 102, at the opposite sides of the heart valve is facilitated. FIGS. 20a-c and 21a-d are schematic illustrations of another example where a section of the first and second support rings 101, 102, have an inverted position in the relaxed state, as illustrated by the inverted section 124 of the second support ring 102, for providing an increased compression force along the anterior portion 114, 114'.

In one example the first and second support rings 101, 102, have a relaxed first state in which the distance (d) between the first and second support rings 101, 102, is substantially zero.

Turning again to FIGS. 1a-b, if the first and second support rings 101, 102, comprises retention units 104, 104', then in the first state the first retention units 104 extend from the first support ring 101 in a direction away from the second support ring 102, as illustrated in FIG. 1a. Further, in the first state, the second retention units 104' extend from the second support ring 102 in a direction away from the first support ring 101, as illustrated in FIG. 1a. In the second state, the first retention units 104 extend from the first support ring 101 in a direction towards the second support ring 102, as shown in FIG. 1b. Further, in the second state, the second retention units 104' extend from the second support ring 102 in a direction towards the first support ring 101. The first and second retention units 104, 104', thus produce a retention force at both of said opposite sides. The retention units 104, 104', are directed towards the valve tissue between the first and second support rings 101, 102, from both of the opposite sides.

As mentioned above, although the examples of the annuloplasty device 100 as schematically illustrated in FIGS. 9-19 show the retention units 104, 104', extending in opposite directions away from each other, to accommodate the change from the relaxed first state, as illustrated in FIG. 1a, to a displaced second state, as illustrated in FIG. 1b, it should be understood that the retention units 104, 104', in the examples of FIGS. 9-19 may be arranged on the first and second support rings 101, 102, to extend towards each other. In the latter case, the position of the first and second support rings 101, 102, should be inverted with respect to the central axis 103. E.g., in a relaxed state of the annuloplasty device 100, the first support ring 101 in the example of FIG. 18b would instead be placed to the right of the second support ring 102, i.e. so that the positions are shifted with respect to axis 103'.

As mentioned, the first support ring 101 may be adapted to be arranged on an atrial side of the heart valve, and the second support ring 102 may be adapted to be arranged on a ventricular side of the heart valve, as exemplified in FIG. 3. FIGS. 5a-b show schematic top-down views where the second ring 102 is shown with dashed lines and the first ring 101 is shown with a solid line. The transition point between the first and second rings 101, 102, is in the example of FIG. 5a at the commissure denoted 302, whereas the transition point between the first and second rings 101, 102, is in the example of FIG. 5b at the commissure denoted 302'. FIGS. 9-21 show examples of an annuloplasty device 100 which may be arranged as illustrated in FIG. 5b.

Further with respect to the examples where the annuloplasty device 100 comprises retention units 104, 104', having retention units 104, 104', at both sides of the valve provides for increasing the retention force and the strength by which the annuloplasty device 100 is fixated at the valve. The retention units 104, 104', may thus engage the tissue from both of the mentioned sides, creating a strong retention force in the radial direction, i.e. perpendicular to the axial direction 103. The first and second supports 101, 102, pinch the tissue from both sides of the valve, so that the retention units 104, 104', a forced into the tissue. The retention units 104, 104', may provide for shaping the annulus as desired even with a reduced pinching force, since the retention units 104, 104', may provide for fixating the shape of the annulus in the radial direction because of the mentioned retention force. This provides for a more reliable implantation at the heart valve, both in the short term and in the long term.

The first and second retention units 104, 104', may extend in opposite directions along the axial direction 103, as schematically illustrated in e.g. FIG. 1a and FIG. 1b. It is conceivable that the first and second retention units 104, 104', may extend with an angle relative the axial direction 103, and further that the aforementioned angle may vary for different retention units 104, 104', along the length of the first and second support rings 101, 102. The angle may vary so that the first and second retention units 104, 104', are extending to securely engage and pierce into the tissue along the length of the first and second support rings 101, 102. The first and second retention units 104, 104', extending away from the first and second support rings 101, 102, should be construed to also encompass variations in the aforementioned angle. The angle in which the retention units extend may vary as further described in the examples below.

In a first state, as mentioned above, the first and second retention units 104, 104', may taper in a direction away from the first and second support rings 101, 102, as illustrated in FIG. 1a. Thus, when the first and second rings 101, 102, are displaced relative to each other and introduced in the shape seen in FIG. 1b at opposite sides of the heart valve leaflets, the first and second retention units 104, 104', have inverted positions with the tapered shape directed towards the opposite support ring 101, 102, to engage the tissue pinched between the first and second support rings 101, 102 (FIG. 3).

The first and second retention units 104, 104', may taper with a cone-shape, as illustrated in the example of FIG. 7b. This provides for an efficient piercing into the tissue while the amount of cutting is minimized, since the first and second retention units 104, 104', tapers to a point. Tissue damage may thus be minimized while a secure anchoring of the first and second support rings 101, 102, is provided. The first and second retention units 104, 104', may further be shaped as truncated cones, as illustrated in the example of FIG. 11c.

The retention units 104, 104', may be integrated with the first and/or second support rings 101, 102, as schematically illustrated in e.g. FIGS. 3, 4, 11a-c, 18a-b. By having retention units 104, 104', integrated with the first and/or second rings 101, 102, a robust, less complex and more readily implementable fixation mechanism can be provided. As illustrated in e.g. FIG. 3, a plurality of retention units 104, 104', may be provided on the respective first and second supports 101, 102. Each individual retention unit 104, 104', may engage or pierce into the tissue with a short distance, for a minimum amount of injury to the tissue. The sum of the retention force and friction created from all the retention units 104, 104', may still provide for a strong fixation into the tissue. The scar healing will be quick since each individual retention unit 104, 104', as relatively small dimensions. This provides for a non-traumatic and still secure fixation of the annuloplasty device 100. Hence, the retention units 104, 104', may provide for tissue fixation at multiple points across the annuloplasty device 100 resulting in reduced forces per fixation point, and no need for bulky stitching device or knotting device. There is further no risk of coronary artery occlusion or coronary sinus perforation. Hence, the annuloplasty device 100 provides for ease of operation, and a less time consuming procedure than stitching.

The first and/or second support rings 101, 102, may be formed from a material with circumferential walls 105 enclosing an interior channel 106 extending in a longitudinal direction 111 of the first and/or second support rings 101, 102. In case the annuloplasty device 100 comprises retention units 104, 104', the latter may extend through respective openings 107 in the circumferential walls 105, as schematically illustrated in FIGS. 7a-b and 11a-c, 18a-b. This provides for a robust fixation of the retention units 104, 104', at the first and/or second support rings 101, 102, due to the support provided by the circumferential walls 105 at the openings 107.

The first and second retention units 104, 104', may extend through the interior channel 106, as schematically illustrated in FIGS. 7a-b. This provides for further increasing the robustness and strength of fixation of the first and second retention units 104, 104'. The first and second retention units 104, 104', may be supported by an inner surface 109 of the interior channel 106, opposite the openings 107, as schematically illustrated in FIG. 7a.

The first and second retention units 104, 104', may have respective attachment points 108 to the inner surface 109 of the interior channel 106, opposite the openings 107. Fixating the first and second retention units 104, 104', to the inner surface 109 provides for a particularly robust anchoring. The first and second retention units 104, 104', may be welded to the respective attachment points 108. The circumferential walls 105 may have a tubular shape enclosing the interior channel 106. Having the first and second support rings 101, 102, formed form a tubular material may provide for desired compression force against the tissue in some applications. In other examples, the first and/or second support rings 101, 102, may have a cross-section which is non-circular, as schematically illustrated in FIGS. 20a-c, 21a-d.

In the examples where the annuloplasty device 100 comprises retention units 104, 104', the retention units 104, 104', may be formed from the material of the circumferential walls 105. This may provide for particularly robust and strong retention units 104, 104', and an overall robust fixation mechanism for the annuloplasty device 100. The retention units 104 may be formed from the material of the first support 101. Similarly, retention units 104' may be formed from the material of the second support 102. The retention units 104, 104', may be cut into shape from the material of the circumferential walls 108. The first and second supports 101, 102, may be integrated and formed from a continuous piece of material. Hence, the retention units 104, 104', may also be formed from such material.

The retention units 104, 104', may be cut to form various shapes for optimizing the gripping force into the tissue. The retention units 104, 104', may be formed by different cutting techniques such as milling or laser cutting techniques. It is also conceivable that the retention units 104, 104', are fixed or integrated onto the respective support rings 101, 102, by other methods, or by being formed from other materials.

Figure 18A:
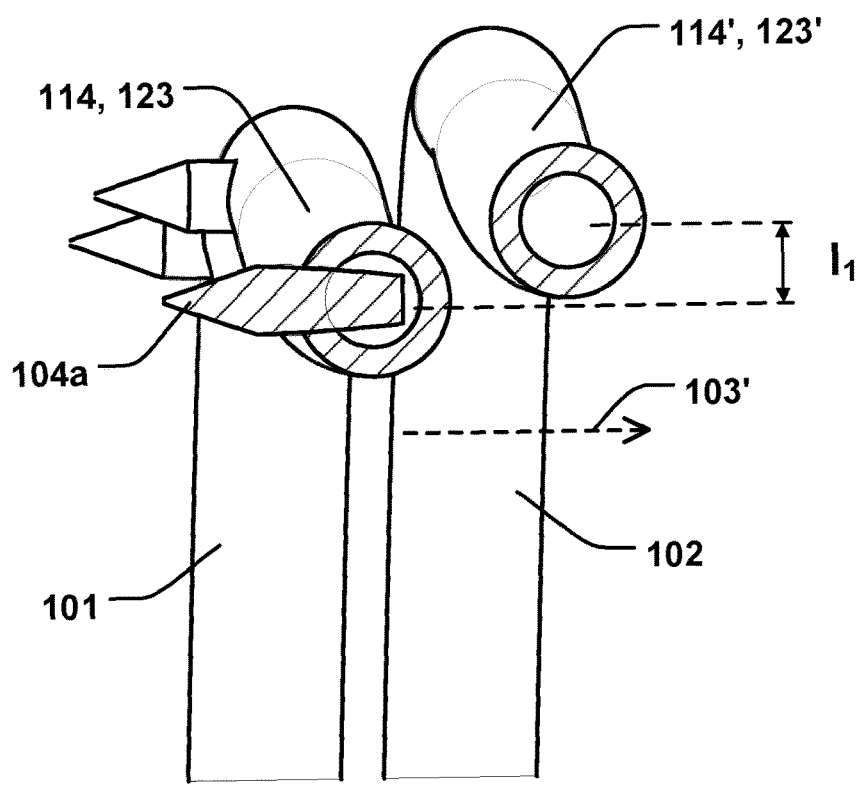
FIG. 18a is a schematic illustration of a detail of an annuloplasty device, at the cross-section A'-A' in FIG. 17a, according to an example of the disclosure.

The first anterior portion 114 may comprises a first plurality 104a of the first retention units 104, and the second anterior portion 114' may comprises a smooth surface free from retention units 104', as schematically illustrated in FIG. 18a. This provides for a secure anchoring into the tissue with the second anterior portion 114 at the atrial side, while at the same time the risk of tissue damage is minimized in the ventricle along the first anterior portion 114.

Figure 18B:
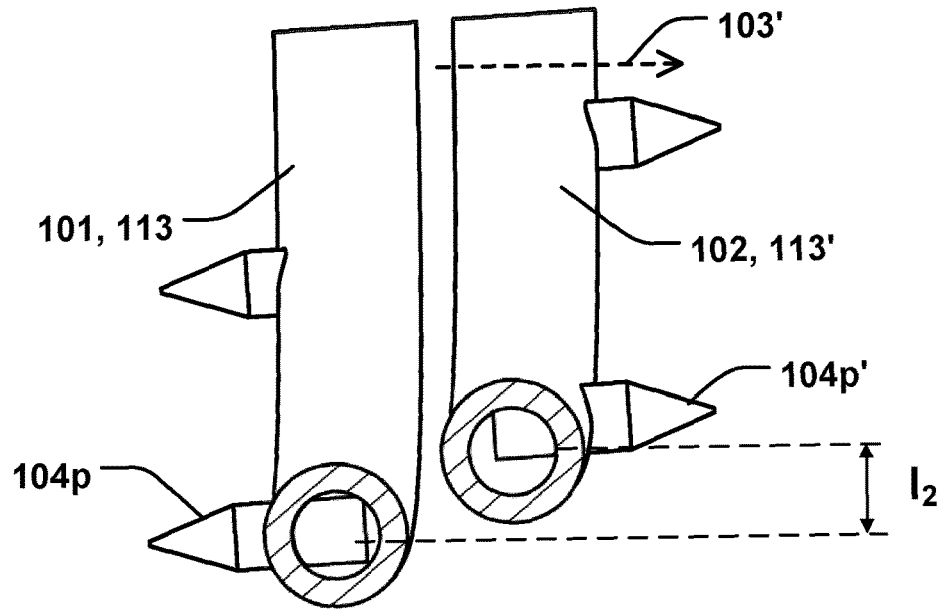
FIG. 18b is a schematic illustration of a detail of an annuloplasty device, at the cross-section B'-B' in FIG. 17a, according to an example of the disclosure.

The first posterior bow 113 may comprise a second plurality 104p of the first retention units 104, as schematically illustrated in e.g. FIG. 17a and in the related cross-section B'-B' in FIG. 18b. The second plurality 104p of the first retention units 104 may taper in a direction extending essentially parallel with the central axis 103. The second plurality 104p of the first retention units 104 on the first support ring 101 may thus extend substantially straight into the tissue, parallel with the central axis 103, along the posterior leaflet on the atrial side.

The second posterior bow 113' may further comprises a second plurality 104p' of the second retention units 104', as schematically illustrated in e.g. FIG. 17b and in the related cross-section B'-B' in FIG. 18b. The second plurality 104p' of the second retention units may taper in a direction extending essentially parallel with the central axis 103. I.e. the retention units 104p, 104p', on the first and second posterior bows 113, 113', may be essentially parallel to each other and to the central axis 103. This provides for a secure fixation to the valve anatomy.

Figure 11A:
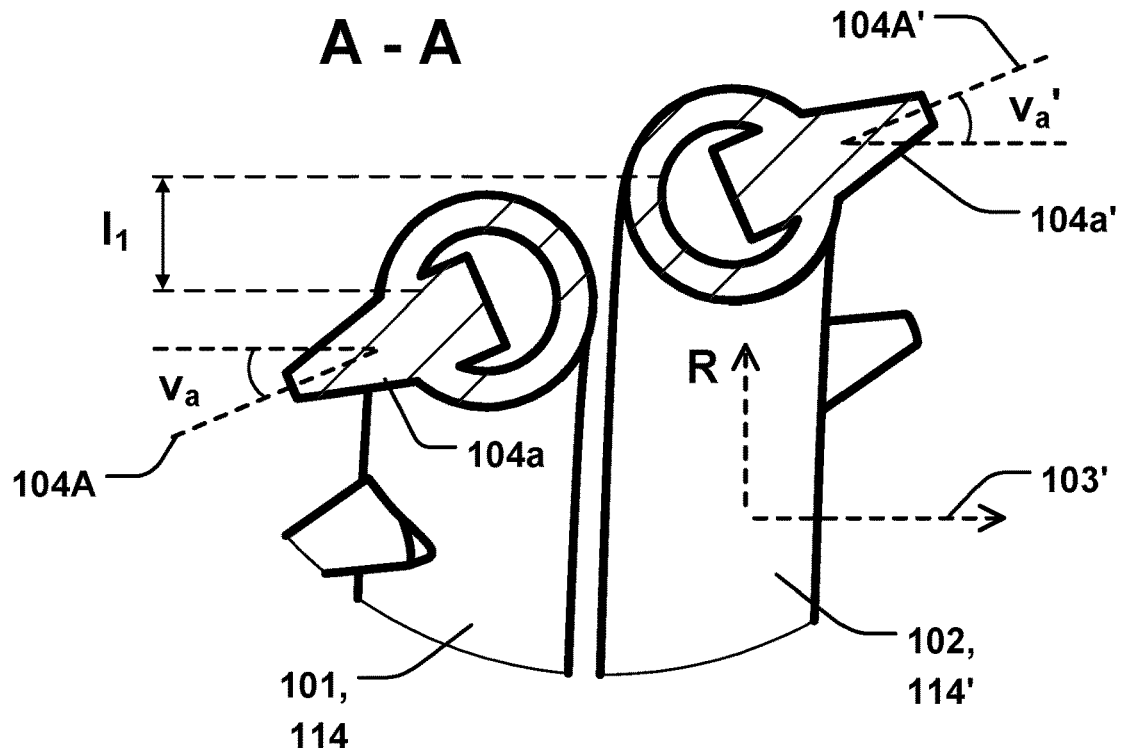
FIG. 11a is a schematic illustration of a detail of an annuloplasty device, at the cross-section A-A in FIG. 10, according to an example of the disclosure.
Figure 11B:
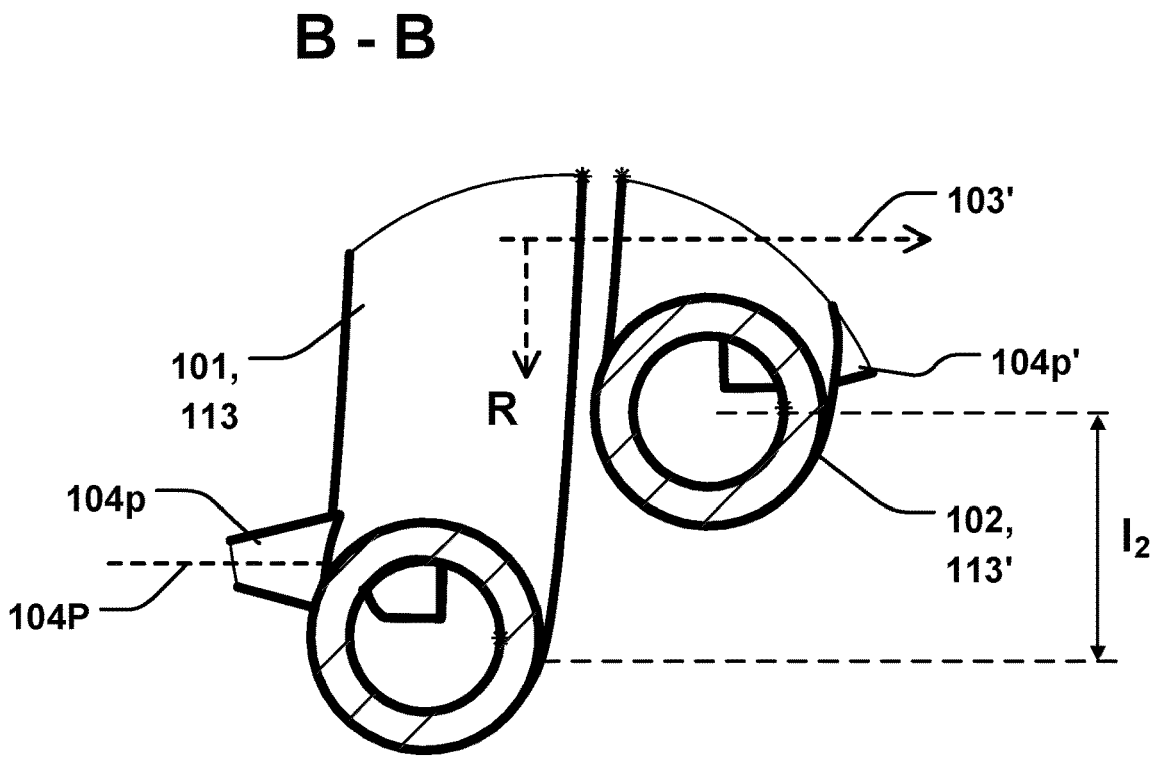
FIG. 11b is a schematic illustration of a detail of an annuloplasty device, at the cross-section B-B in FIG. 10, according to an example of the disclosure.
Figure 14:
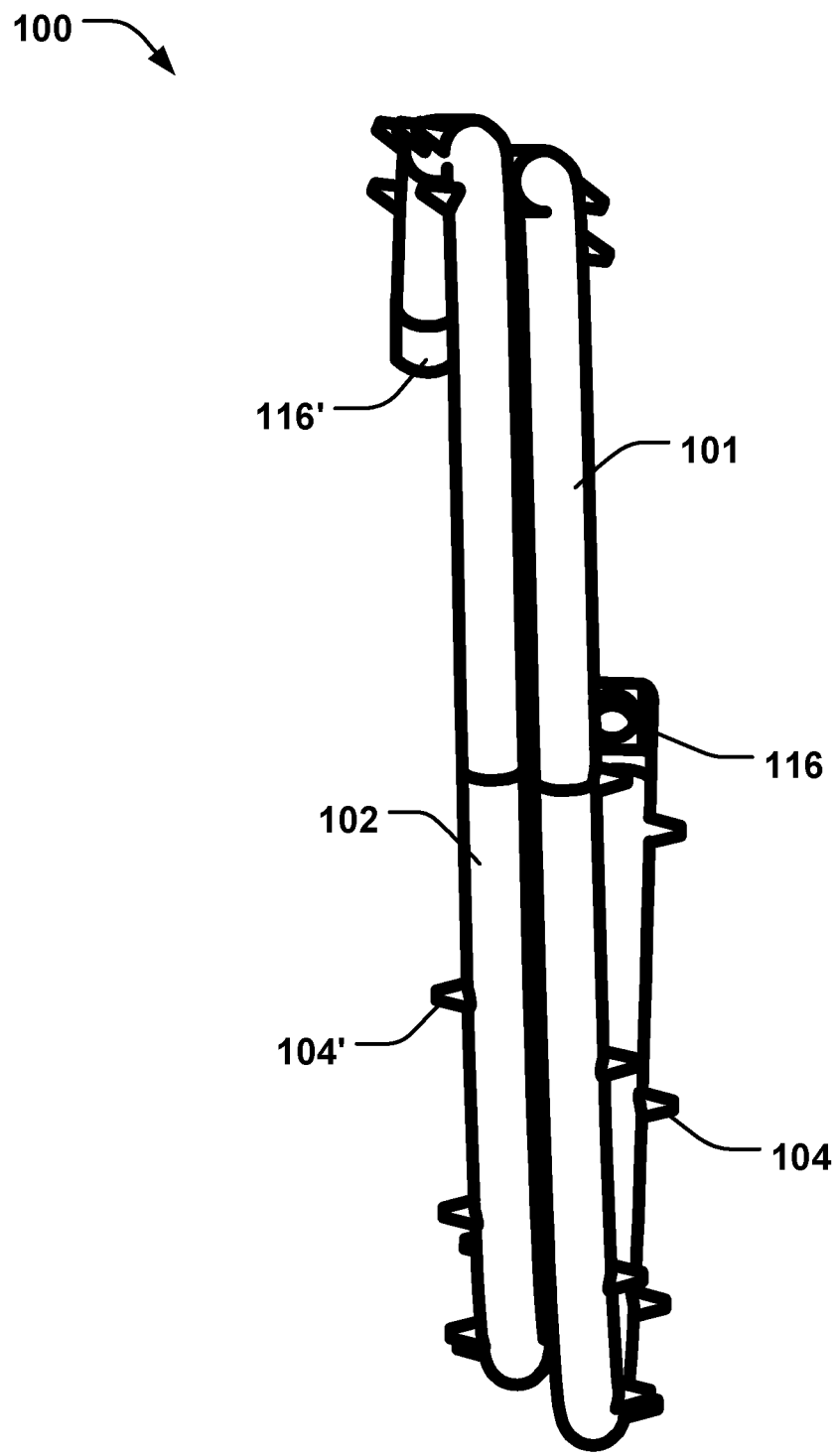
FIG. 14 is a schematic illustration of an annuloplasty device, in a side view of FIG. 10 along the vertical direction Y, and from an opposite side compared to FIG. 12, according to an example of the disclosure.
Figure 15:
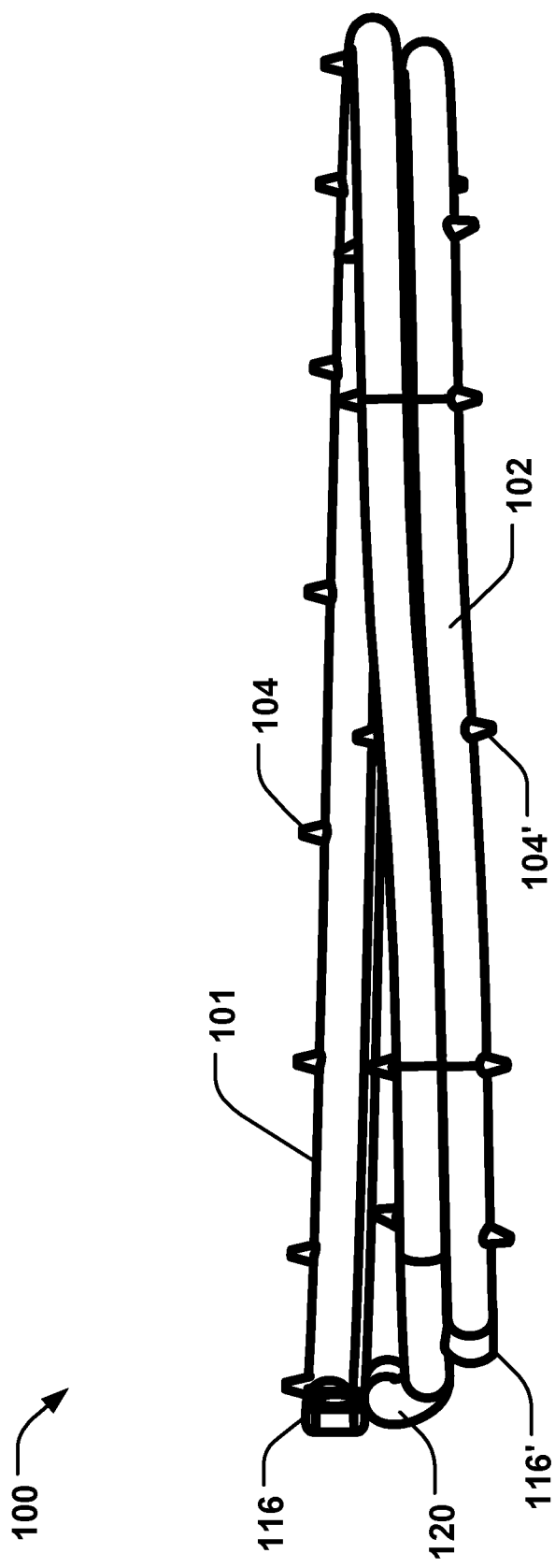
FIG. 15 is a schematic illustration of an annuloplasty device, in a side view of FIG. 10 along the horizontal direction X, according to an example of the disclosure.

Turning to the example in FIGS. 11a-b and 16, the first anterior portion 114 may comprises a first plurality 104a of the first retention units 104. The first plurality 104a of the first retention units may taper in a first direction 104A forming a first angle ($v_a$) with the central axis 103, as schematically illustrated in FIG. 16 and in the related cross-section A-A in FIG. 11a. In one example, the annuloplasty device 100 in FIGS. 9-16 is in the aforementioned relaxed first state. I.e. as seen in e.g. FIGS. 11a and 16, the retention units 104a, 104a', extend in directions away from each other, whereas in the displaced second state the first and second support rings 101, 102, will be displaced so that their relative positions are shifted and the retention units 104a, 104a', extends towards each other. On another example however, as described above, the first and second support rings 101, 102, are not inverted in the relaxed state. Having the first plurality 104a of the first retention units 104 extending with an angle ($v_a$) relative the central axis 103 provides in some applications for an improved anchoring into the tissue at the anterior leaflet on the atrial side.

The first direction 104A may extend at least partly radially inwards towards the central axis 103, i.e. opposite direction (R) as indicated schematically in FIG. 11a. The first plurality 104a of the first retention units 104 may this grip into the tissue with an angle radially inwards, and the risk for dislocation by a force acting radially inwards on the first support ring 101 may thus minimized in some procedures.

The first posterior bow 113 may comprise a second plurality 104p of the first retention units 104, as schematically illustrated in e.g. FIG. 16 and in the related cross-section B-B in FIG. 11b. The second plurality 104p of the first retention units 104 may taper in a second direction 104P extending essentially parallel with the central axis 103. The second plurality 104p of the first retention units 104 on the first support ring 101 may thus extend substantially straight into the tissue, parallel with the central axis 103, along the posterior leaflet on the atrial side. Having a combination of straight retention units 104p on the posterior bow 113 and angled retention units 104a on the anterior portion 114 provides for an effective yet facilitated anchoring into the tissue in some procedures and anatomies.

The second anterior portion 114' may comprises a first plurality 104a' of the second retention units 104', as schematically illustrated in e.g. FIG. 16 and in the related cross-section A-A in FIG. 11a. The first plurality 104a' of the second retention units may taper in a second direction 104A' forming a second angle ($v_a'$) with the central axis 103. The second direction 104A' may extend at least partly radially outwards towards a radial direction (R), as indicated in FIG. 11a. The radial direction (R) is perpendicular to the central axis 103. The second support ring 102 will in the displaced second state be arranged in the ventricle, thus the first plurality 104a' of the second retention units 104' will extend with the second angle ($v_a'$) radially outwards into the tissue at the ventricular side along the anterior leaflet. This provides of an efficient anchoring into the aortoseptal wall in some procedures. In one example, having a combination of retention units 104a on the anterior portion 114 of the first support ring 101 being angled radially inwards and retention units 104a' on the anterior portion 114' of the second support ring 101 being angled radially outwards provides for an effective anchoring and retention of the annuloplasty device 100 on the opposite sides of the valve 100.

The second posterior bow 113' may further comprises a second plurality 104p' of the second retention units 104', as schematically illustrated in e.g. FIG. 16 and in the related cross-section B-B in FIG. 11b. The second plurality 104p' of the second retention units may taper in a second direction 104P' extending essentially parallel with the central axis 103. I.e. the retention units 104p, 104p', on the first and second posterior bows 113, 113', may be essentially parallel to each other and to the central axis 103.

The first and second anterior portions 114, 114', may comprise retention units 104, 104', arranged adjacent the "tricone areas" of the mitral valve, adjacent the commissures 302, 302'. Gripping and fixation into the tissue at these areas provides for a robust and secure anchoring of the annuloplasty device 100 to the heart valve. The retention units 104, 104', may be evenly spaced along at least part of the first and/or second anterior portions 114, 114', as exemplified in FIGS. 16 and 17a. Such even distribution of the fixation points provides for a reliable anchoring to the tissue, minimizing the risk of localized pressure peaks. It should be understood however that the distance between each of the retention units 104, 104', may be varied to optimize the anchoring annuloplasty device 100 to different anatomies. The first and/or second anterior portion 114, 114', may have 5 to 6 retention units 104, 104', respectively. The first and/or second posterior portion 113, 113', may have 6 to 8 retention units 104, 104', respectively. This may provide for a particularly efficient fixation to the tissue while minimizing the overall tissue penetration. It should be understood however that the number of retention units 104, 104', may be varied to optimize the anchoring annuloplasty device 100 to different anatomies and valves of different size. In one example the length of the retention units 104, 104', is in the range 0.5-1.5 mm. In another example the length of the retention units 104, 104', is in the range 0.8-1.2 mm, such as 1.0 mm, which may provide for a particularly advantageous fixation into the tissue while being easy to deploy via a delivery catheter.

The advantageous features of the retention units 104, 104', described in relation to FIGS. 9-19 provides for an improved annuloplasty device 100 with a facilitated anchoring into the tissue, also in absence of the aforementioned displacement (d) in the relaxed state. I.e. in this case, the annuloplasty device 100 has a relaxed state corresponding to the illustration in FIG. 1b. I.e. the retention units 104, 104', points in a direction towards each other in the relaxed state. The shape and positioning of the retention units 104, 104', thus also provides for a separate aspect of the invention.

As mentioned, the first support ring 101 may comprise a first posterior bow 113 and the second support ring comprises a second posterior bow 113'. The first and second posterior bows 113, 113', may be adapted to conform to a posterior aspect of the heart valve. The first and second posterior bows 113, 113', may be separated by an intermediate anterior portion 114. Although the advantages of having retention units 104, 104', on the anterior portions 114, 114', has been described with respect to the examples of FIGS. 11a and 16, it is conceivable that the anterior portion 114 may comprise a smooth surface, as described above with respect to the example in 18a. I.e. the smooth surface may be free from retention units 104, 104'. A further example is illustrated in FIG. 4, showing the rings 101, 102, in a stretched configuration. The retention units 104, 104', may thus be arranged on respective first and second posterior bows 113, 113'. The first and second retention units 104, 104', may be arranged with an off-set distance 115 from the anterior portion 114 towards respective first and second posterior bows 113, 113'. Thus, the anterior portion 114 may comprise a smooth surface free from retention units 104, 104'. I.e. the first and second retention units 104, 104', may be arranged with an off-set distance 115 from the anterior portion 114 towards respective first and second posterior bows 113, 113'. The off-set distance 114 may be varied to optimize the annuloplasty device 100 to the particular. The first support 101 may have the retention units 104 extending in a first direction, and the second support 102 may have the retention units 104' extending in an opposite direction.

The position of the first retention units 104 may be off-set in the radial direction (perpendicular to the axial direction 103) with respect to the second retention units 104'. Thus, although both the first and second retention units 104, 104', may extend in the vertical direction, the risk of having the first retention units 104 to engage with the second retention units 104' is avoided, which otherwise may lead to fully penetrating the valve tissue. This may be realized by having different diameters of the support rings 101, 102, and/or by arranging the first and second retention units 104, 104', to extend from opposite sides of the respective support rings 101, 102.

It should be understood that in one example only the first or second support ring 101, 102, may comprise retention units 104, 104'. In a further example, the annuloplasty device 100 do not comprise any retention units 104, 104', as illustrated in FIGS. 20a-c, 21a-d. In the examples of FIGS. 20a-c, 21a-d, the curvature or position of the first and second support rings 101, 102, may be carefully tailored to the anatomy, due to the transition section 120, to provide a secure position of the annuloplasty device 100 also in absence of retention units 104, 104'.

In some examples, the first and/or second support rings 101, 102, may have a cross-section which is non-circular, as schematically illustrated in FIGS. 20a-c, 21a-d. The first and/or second support rings 101, 102, may be formed from a solid material without an interior channel 106, which may have a non-circular cross-section. Having a non-circular shape provides for increasing the compression force between the first and second rings 101, 102, in the coiled configuration while maintaining a compact cross-sectional profile of the first and second rings 101, 102. The dimensions of the sides of the cross-section may be varied in order to provide for an optimized bending resistance of the support rings 101, 102. The cross-section may be essentially rectangular.

The cross-section may vary along a longitudinal direction 111 of the first and/or second support ring 101, 102. Varying the aforementioned dimensions of the sides (e.g. the sides of a rectangle) along the length of the first and second support rings 101, 102, i.e. along the longitudinal direction 111, allows for varying the flexibility of the rings 101, 102, along the longitudinal direction 111 and be customized to different anatomical positions around the annulus of the heart valve. This provides for better accommodating movement of the tissue which may be greater at localized sections of the annulus, while other sections may have an increased rigidity for a stronger pinching effect between the first and second support rings 101, 102. A more secure and robust positioning of the device 100 may thus be provided and improved long-term functioning. A varying cross-section provides also for optimizing the flexibility with respect to the delivery and positioning phase of the annuloplasty device 100. E.g. portions of the first and second support rings 101, 102, which are subject to the most bending movement when being inserted in a delivery catheter, such as the commissure sections 113'b, 113'c, (see e.g. FIG. 20c) may have a cross-section which increases the flexibility, e.g. by having a reduced area and/or reduced width in the direction in which the support ring 101, 102, is bent.

FIGS. 20a-c, 21a-d are schematic illustrations of a further example of an annuloplasty device 100 comprising a transition section 120 providing for the advantageous benefits as described above with respect to FIGS. 1-19.

The second anterior portion 114' may comprise an inverted section 124 extending in parallel with the first and second coil planes 101', 102'. The inverted section 124 and the second posterior bow 113' extend on opposite sides of the first support ring 101 with respect to the direction of the central axis 103, as schematically illustrated in e.g. the side view of FIG. 21*d* and the perspective view of FIG. 20*b*. Having a section of the second anterior portion 114' raised above the first support ring 101, i.e. above the first anterior portion 114 as illustrated in FIG. 20*b*, provides for increasing the compression force along the anterior portions 114, 114', when the first and second support rings 101, 102, are arranged on opposite sides of the heart valve. When the annuloplasty device 100 is positioned at the heart valve, with the second support ring 102 arranged in the atrial side, the inverted section 124 will be pushed down, i.e. against the direction of the central axis 103 in FIG. 20*b*, when forced into place at the heart valve. The anterior portion 114' will thus also be placed at the atrial side of the heart valve. Having an inverted section 124 in the relaxed state of the annuloplasty device 100 means that the second anterior portion 114' will strive towards the relaxed shape, free from outside forces, as illustrated in e.g. FIG. 20*b*. The inverted section of the second anterior portion 114' will thus strive to a position above the first anterior portion 114 (as shown in FIG. 20*b*), with respect to the central axis 103. This will cause an increased pressure on the valve tissue along the inverted section 124, and between the first and second anterior portions 114, 114', when the annuloplasty device 100 is implanted. This provides for a more secure fixation of the annuloplasty device 100 at the heart valve.

The first and second support rings 101, 102, have respective first and second free ends 116, 116', configured to be arranged on opposite sides of the native heart valve leaflets, as described above. In one example, the inverted section 124 transitions to the free end 116' of the second support ring 102 over an anterior transition section 125, as schematically illustrated in the side view of FIG. 21*d* and the perspective view of FIG. 20*b*. The anterior transition section 125 bends at least partly along the central axis 103 so that the free end 116' of the second support ring 102 is arranged on the same side of the first support ring 101 as the second posterior bow 113', with respect to the direction of the central axis 103. Having the free end 116' recessed from the inverted section, against the direction of the central axis 103, provides for a further improved accommodation to the anatomy of the heart valve. For example, the free end 116' may be positioned to sit in the subannular groove by having such anterior transition section 125. The anterior transition section 125 may be arranged at the end of the first and second anterior portions 114, 114', in a direction towards the free end 116', as exemplified in FIG. 20*b*. The second support ring 102 may comprise a free end 116' which is curved towards the free end 116 of the first support ring 101, in the plane of coil planes 101', 102', as further exemplified in FIGS. 20*a-b*. The second support ring 102 may thus be bent after the second anterior portion 114', i.e. adjacent the position of the commissure. In one example, the anterior transition section 125 is arranged towards the end of the second anterior portion 114', in a direction towards the free end 116', so that essentially the entire curved part of the second support ring 102, after the second anterior portion 114', is arranged at the same side of the first support ring 101 as the second posterior bow 113' with respect to the direction of the central axis 103. This provides in some examples for an improved fit to the surrounding anatomy of the annuloplasty device 100.

The second anterior portion 114' may comprise a second anterior transition section 126, where the second support ring 102 is bent in a direction along the central axis 103 to form the step-up curve of the inverted section 124, as exemplified in FIG. 20*b*. The step-down curve of the inverted section 124, towards the free end 116', may consequently be formed by the anterior transition section 125 described above. The advantageous features of the inverted section 124, and anterior transition sections 125, 126, described in relation to FIGS. 20*a-c*, 21*a-d*, provides for an improved annuloplasty device 100 with a stronger retention into the tissue, also in absence of the aforementioned transition section 120. The inverted section 124 thus also provides for a separate aspect of the invention.

In the examples of FIGS. 20*a-c*, 21*a-d*, the length of the first and second support rings 101, 102, form essentially two complete loops. This provides in some examples for an improved anchoring of the annuloplasty device 100 to the heart valve. In some situations, an off-set distance 117 as described in relation to FIG. 6 may be advantageous.

The second posterior bow 113' may comprise a central posterior arch 113'*a*, and further a first commissure section 113'*b* and a second commissure section 113'*c* on either side of the central posterior arch 113'*a*, as schematically illustrated in FIGS. 20*c* and 21*c-d*. The first support ring 101 transitions to the first commissure section 113'*b* over the transition section 120, and the second commissure section 113'*c* connects to the second anterior portion 114'. In one example, a separation distance ($d_2$) between the first support ring 101 and the central posterior arch 113'*a*, along the central axis 103, is less than a separation distance ($d_1$, $d_3$) between the first support ring 101 and any of the first and second commissure sections 113'*b*, 113'*c*. The side view of FIG. 21*c* is a schematic illustration showing a reduced distance ($d_2$) between the first and second support rings 101, 102, compared to the distance ($d_1$, $d_3$) along any of the first and second commissure sections 113'*b*, 113'*c*. This provides for an improved compression between the first and second support rings 101, 102, along the central posterior arch 113'*a*. The fixation of the annuloplasty device 100 may thus be facilitated. At the same time, the larger separation distance ($d_1$, $d_3$) at the first and second commissure sections 113'*b*, 113'*c*, can provide for a more reliable fit to the tissue at the commissure anatomy of the heart valve, e.g. as described above with respect to having the separation distance ($d_1$) at the transition section 120.

In one example, a separation distance ($d_1$) between the first commissure section 113'*b* and the first support ring 101 is larger than a separation distance $d_3$ between the second commissure section 113'*c* and the first support ring 101. FIG. 21*c* show an example of such increased separation distance ($d_1$). Hence, as described above with respect to the transition section 120, this provides for an improved fit to the anatomy where the first support ring 101 extends through the commissure and transitions to the second support ring 102 on the opposite side of the heart valve. In one example the separation distances $d_2$ and $d_3$ may be essentially the same.

The advantageous features of the relation between separation distances ($d_1$, $d_2$, $d_3$) described in relation to FIGS. 21*b-c*, 21*a-d*, provides for an improved annuloplasty device 100 with a more secure anchoring into the tissue, also in absence of the aforementioned inverted section 124. The separation distances ($d_1$, $d_2$, $d_3$) thus also provides for a separate aspect of the invention.

The first and second support rings 101, 102, may have respective free ends 116, 116', as illustrated in FIG. 6. The free ends 116, 116', may be configured to be arranged on opposite sides of the native heart valve leaflets. The two free ends 116, 116', may be displaced from each other with a peripheral off-set distance 117 extending in a coil plane 118, as schematically illustrated in FIG. 6. The coil plane 118 is substantially parallel to an annular periphery 119 of the coil formed by the first and second support rings 101, 102, and perpendicular to the axial direction 103. The coil plane 118 accordingly corresponds to the plane spanned by the annular periphery 119 of the device 100 when in the coiled configuration. The peripheral off-set distance 117 between the two free ends 116, 116', thus extends substantially perpendicular to the central axis 103. This means that, when the device 100 is positioned in the implanted state, around the annulus of the heart valve, the two free ends 116, 116', will be separated along the plane of the valve. Having such off-set 117 in the plane of the valve, resulting in a reduced length of the first or second support rings 101, 102, may be advantageous in some anatomies where there might be a risk of interference with the valve motion. In the example of FIG. 6 the off-set 117 extends along the anterior portion 114. In another example, such as schematically illustrated in FIGS. 16 and 17a, the length of the off-set 117 is reduced and instead extending along part of the posterior bow 113. This provides in some applications for an enhanced anchoring strength to the tissue as the tissue is pinched along both anterior portions 114, 114', further in combination with having retention units 104, 104', on at least one of the anterior portions 114, 114'. A compression force between the first and second rings 101, 102, may in this example also be exerted onto the "tricone" areas of the valve, adjacent the commissures 302, 302'. In the example of FIGS. 16 and 17a, the total circumference of the first and second rings 101, 102, may be approximately 710 degrees. The off-set 117 may be removed in some examples, to have a complete 720 degrees of the turns of the first and second support rings 101, 102, e.g. as illustrated in examples of FIGS. 20a-c, 21a-d.

A proximal connector element 121 may be fixed to the free end 116 of the first support ring 101. The example in FIG. 13 shows a connector element 121 comprising an aperture for interlocking with a delivery catheter. Different types of connector elements may be provided at the free end 116. The distal end 116' of the second support ring 102 may be shaped with a blunt tip to reduce the risk of damaging the tissue, see FIG. 12.

Figure 8:
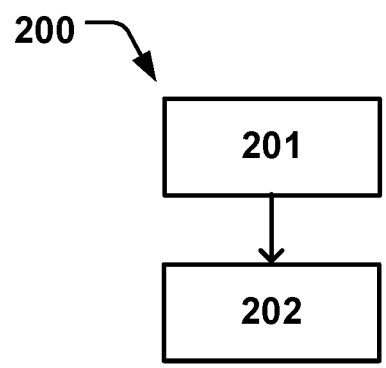
FIG. 8 is a flow chart of a method of repairing a defective heart valve, according to an example of the disclosure.
Figure 9:
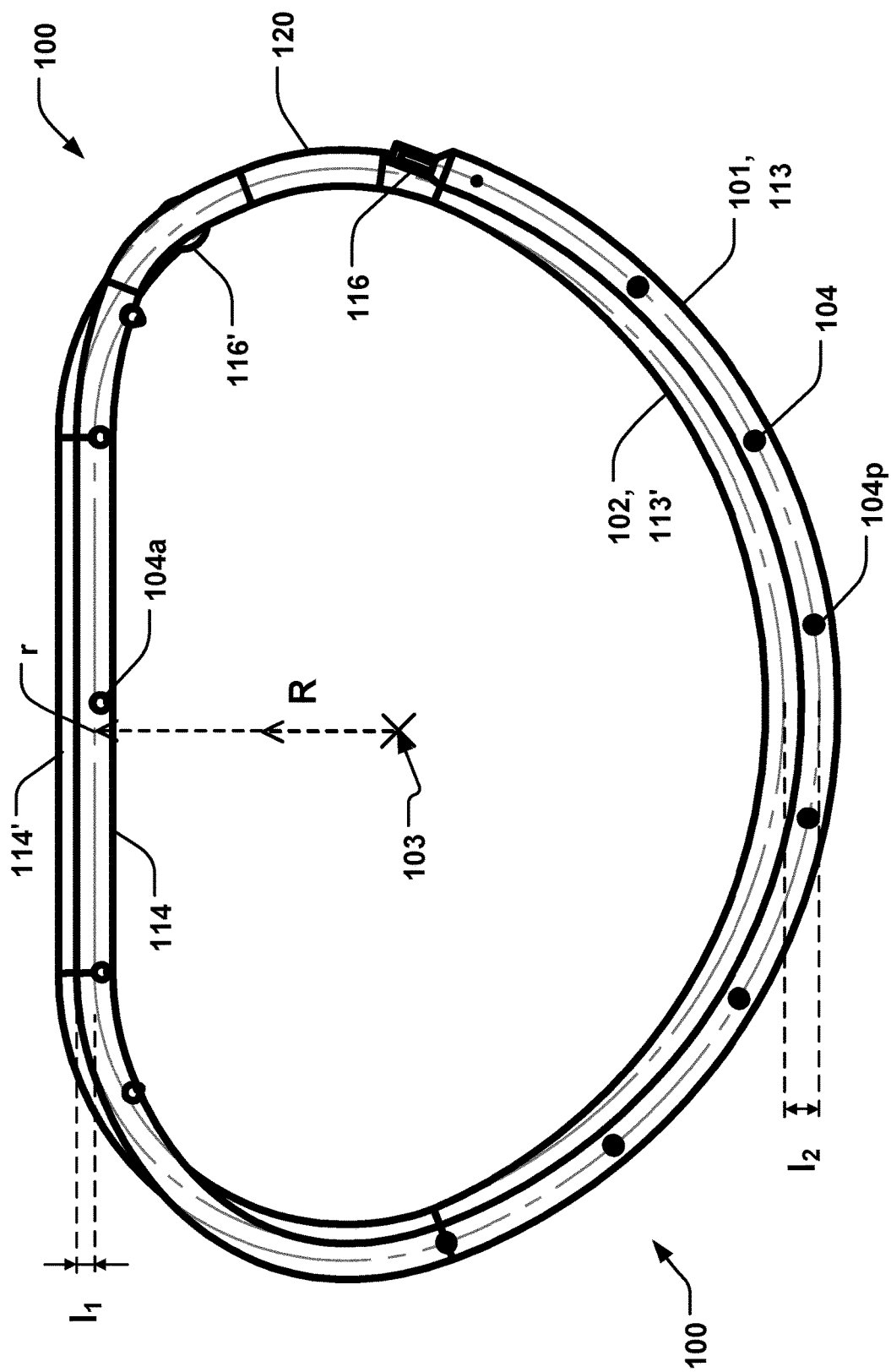
FIG. 9 is a schematic illustration of an annuloplasty device, in a top-down view, according to an example of the disclosure.
Figure 10:
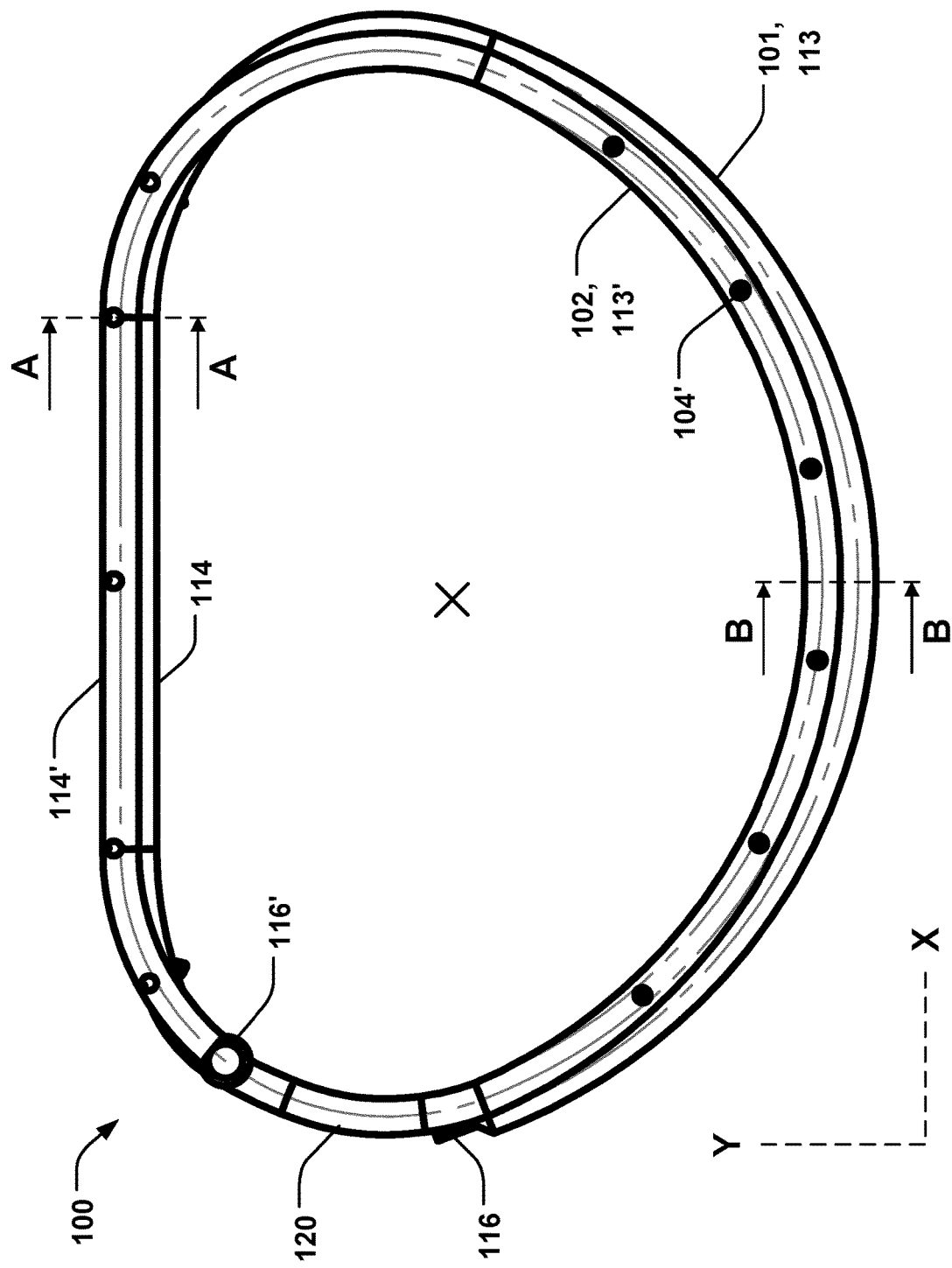
FIG. 10 is a schematic illustration of an annuloplasty device, in a top-down view and from an opposite side of the annuloplasty device of the view in FIG. 9, according to an example of the disclosure.

A method 200 of repairing a defective heart valve is disclosed. The method 200 is schematically illustrated in FIG. 8, in conjunction with FIGS. 1-7, and FIGS. 9-21. The order in which the steps are described should not be construed as limiting, and it is conceivable that the order of the steps may be varied depending on the particular procedure. The method 200 comprises positioning 201 a second support ring 102 of an annuloplasty device 100 on a ventricular side of the heart valve. The method 200 comprises positioning 202 a first support ring 101 of the annuloplasty device 100 on an atrial side of the heart valve. The first and second support rings 101, 102, are arranged as a coil around a central axis 103 on opposite sides of native heart valve leaflets of the heart valve. The first and second support rings 101, 102, are positioned so that the first support ring 101 transitions to the second support ring 102 over a transition section 120 positioned at a commissure 302, 302', of the heart valve leaflets. The first and second support rings 101, 102, extend in respective first and second coil planes 101', 102', being essentially perpendicular to the central axis 103. The transition section 120 bends at least partly along the central axis 103 so that the first coil plane 101' is separated a distance ($d_1$) from the second coil plane 102' along the central axis 103 at the transition section 120. The method 200 provides for the advantageous benefits as discussed above in relation to the annuloplasty device 100 and FIGS. 1-21. The method 200 allows for a facilitated anchoring of the annuloplasty device 100 at the heart valve, due to the improved accommodation to the surrounding anatomy at the heart valve and increased compression force between the first and second support rings 101, 102, without the need to apply sutures, clips or other external fastening devices.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. An annuloplasty device comprising a first support ring and a second support ring having a coiled configuration in which the first and second support rings are arranged as a coil around a central axis, wherein the first and second support rings are configured to be arranged on opposite sides of native heart valve leaflets of a heart valve, wherein the first support ring transitions to the second support ring over a transition section, wherein the transition section is adapted to be arranged at a commissure of the heart valve leaflets, wherein the first and second support rings extend in respective first and second coil planes being essentially perpendicular to the central axis, wherein the transition section bends at least partly along the central axis so that the first coil plane is separated a distance (d1) from the second coil plane along the central axis at the transition section, wherein the first support ring comprises a first posterior bow and a first anterior portion, the second support ring comprises a second posterior bow and a second anterior portion, the first and second posterior bows are adapted to conform to a posterior aspect of said heart valve, and the first and second anterior portions are adapted to conform to an anterior aspect of said heart valve, wherein the second anterior portion comprises an inverted section extending in parallel with the first and second coil planes, wherein the inverted section and the second posterior bow extend on opposite sides of the first support ring with respect to the direction of the central axis.

2. The annuloplasty device according to claim 1, wherein the first support ring is adapted to be arranged on an atrial side of said heart valve, and the second support ring is adapted to be arranged on a ventricular side of the heart valve.

3. The annuloplasty device according to claim 1, wherein the transition section bends at least partly along a radial direction (R), the radial direction being perpendicular to the central axis so that the transition section is concave towards the radial direction.

4. The annuloplasty device according to 1, wherein at least part of the first anterior portion and/or the second anterior portion is curved to form a respective concave section being concave towards a radial direction (R), the radial direction being perpendicular to the central axis.

5. The annuloplasty device according to claim 1, wherein the first anterior portion is displaced a distance (I1) from the second anterior portion along a radial direction (R) so that at least part of the second anterior portion extends with a greater radius (r) from the central axis than the first anterior portion, the radial direction being perpendicular to the central axis.

6. The annuloplasty device according to claim 1, wherein the first posterior bow is displaced a distance (l2) from the second posterior bow along a radial direction (R), the radial direction being perpendicular to the central axis.

7. The annuloplasty device according to claim 6, wherein at least part of the first posterior bow extends with a greater radius (r) in the radial direction (R) from the central axis than the second posterior bow.

8. The annuloplasty device according to claim 1, wherein the first and second support rings have respective first and second free ends configured to be arranged on opposite sides of the native heart valve leaflets, the inverted section transitions to the free end of the second support ring over an anterior transition section,
   wherein the anterior transition section bends at least partly along the central axis so that the free end of the second support ring is arranged on the same side of the first support ring as the second posterior bow, with respect to the direction of the central axis.

9. The annuloplasty device according to claim 1, wherein the second posterior bow comprises a central posterior arch and a first commissure section and a second commissure section on either side of the central posterior arch,
   wherein the first support ring transitions to the first commissure section over the transition section, and the second commissure section connects to the second anterior portion and
   wherein a separation distance (d2) between the first support ring and the central posterior arch, along the central axis, is less than a separation distance (d1, d3) between the first support ring and any of the first and second commissure sections.

10. The annuloplasty device according to claim 9, wherein a separation distance (d1) between the first commissure section and the first support ring is larger than a separation distance (d3) between the second commissure section and the first support ring.

11. The annuloplasty device according to claim 1, wherein the first support ring comprises first retention units and the second support ring comprises second retention units, wherein the first retention units and the second retention units extend in opposite directions along the axial direction.

12. The annuloplasty device according to claim 11, wherein the first and second support rings having a separation distance (d) and are movable relative to each other along the central axis to vary said separation distance,
wherein the first and second support rings comprises a resilient shape-memory material and are movable along the central axis from a relaxed first state to a displaced second state, whereby, in the first state;
   the first retention units extend from the first support ring in a direction away from the second support ring, and
   the second retention units extend from the second support ring in a direction away from the first support ring, and
wherein, in the second state;
   the first retention units extend from the first support ring in a direction towards the second support ring, and
   the second retention units extend from the second support ring in a direction towards the first support ring,
whereby the first and second support rings strive to assume the first state when displaced to the second state to pinch the valve leaflets from the opposite sides, in use, and the first and second retention units to produce a retention force at both of said opposite sides.

13. The annuloplasty device according to claim 11, wherein the first and second retention units tapers with a cone-shape.

14. The annuloplasty device according to claim 1, wherein:
   the first support ring comprises a first posterior bow and a first anterior portion,
   the second support ring comprises a second posterior bow and a second anterior portion, and
   the first and second posterior bows are adapted to conform to a posterior aspect of said heart valve, and the first and second anterior portions are adapted to conform to an anterior aspect of said heart valve,
   wherein the first anterior portion comprises a first plurality of retention units, and
   wherein the second anterior portion comprises a smooth surface free from retention units.

15. The annuloplasty device according to claim 14, wherein the first posterior bow comprises a second plurality of the first retention units and the second plurality of the first retention units taper in a direction extending essentially parallel with the central axis,
   wherein the second posterior bow comprises a second plurality of the second retention units, and the second plurality of the second retention units tapers in a direction extending essentially in parallel with the central axis.

* * * * *